US009925142B2

United States Patent
Daftarian et al.

(10) Patent No.: US 9,925,142 B2
(45) Date of Patent: *Mar. 27, 2018

(54) USE OF LIPOSOMES IN A CARRIER COMPRISING A CONTINUOUS HYDROPHOBIC PHASE AS A VEHICLE FOR CANCER TREATMENT

(71) Applicant: IMMUNOVACCINE TECHNOLOGIES INC., Halifax (CA)

(72) Inventors: Pirouz M. Daftarian, Halifax (CA); Marc Mansour, Halifax (CA); Bill Pohajdak, Dartmouth (CA); Robert G. Brown, Dartmouth (CA); Wijbe M. Kast, Flintridge, CA (US)

(73) Assignee: IMMUNOVACCINE TECHNOLOGIES INC., Halifax (CA)

( * ) Notice: Subject to any disclaimer, the term of this patent is extended or adjusted under 35 U.S.C. 154(b) by 134 days.

This patent is subject to a terminal disclaimer.

(21) Appl. No.: 14/674,063

(22) Filed: Mar. 31, 2015

(65) Prior Publication Data
US 2015/0202152 A1   Jul. 23, 2015

Related U.S. Application Data

(62) Division of application No. 12/083,209, filed as application No. PCT/CA2006/001640 on Oct. 5, 2006, now abandoned.

(60) Provisional application No. 60/806,573, filed on Jul. 5, 2006.

(30) Foreign Application Priority Data

| Oct. 7, 2005 | (CA) | 2523032 |
| Jan. 13, 2006 | (CA) | 2533705 |
| Apr. 7, 2006 | (CA) | 2542212 |

(51) Int. Cl.
| A61K 45/06 | (2006.01) |
| A61K 9/127 | (2006.01) |
| A61K 9/00 | (2006.01) |
| A61K 31/4745 | (2006.01) |
| A61K 39/00 | (2006.01) |
| A61K 39/12 | (2006.01) |
| A61K 39/385 | (2006.01) |
| C07K 14/005 | (2006.01) |
| C07K 14/47 | (2006.01) |
| C12N 9/90 | (2006.01) |
| A61K 47/64 | (2017.01) |

(52) U.S. Cl.
CPC ............ *A61K 9/127* (2013.01); *A61K 9/0024* (2013.01); *A61K 31/4745* (2013.01); *A61K 39/00* (2013.01); *A61K 39/0011* (2013.01); *A61K 39/12* (2013.01); *A61K 39/385* (2013.01); *A61K 47/646* (2017.08); *C07K 14/005* (2013.01); *C07K 14/4748* (2013.01); *C12N 9/90* (2013.01); *A01K 2267/0331* (2013.01); *A61K 2039/545* (2013.01); *A61K 2039/55544* (2013.01); *A61K 2039/55555* (2013.01); *A61K 2039/55561* (2013.01); *A61K 2039/55566* (2013.01); *A61K 2039/585* (2013.01); *A61K 2039/6031* (2013.01); *A61K 2039/6037* (2013.01); *A61K 2039/622* (2013.01); *A61K 2039/627* (2013.01); *A61K 2039/70* (2013.01); *C07K 2319/00* (2013.01); *C12N 2710/20022* (2013.01); *C12N 2710/20034* (2013.01); *C12Y 503/03012* (2013.01)

(58) Field of Classification Search
None
See application file for complete search history.

(56) References Cited

U.S. PATENT DOCUMENTS

| 5,015,476 A | 5/1991 | Cohrum et al. |
| 5,340,588 A | 8/1994 | Domb |
| 5,422,109 A | 6/1995 | Brancq et al. |
| 5,637,300 A | 6/1997 | Dunbar et al. |
| 5,662,931 A | 9/1997 | Munechika et al. |
| 5,705,151 A | 1/1998 | Dow et al. |
| 5,709,879 A | 1/1998 | Barchfeld et al. |
| 5,736,141 A | 4/1998 | Brown et al. |
| 5,820,879 A | 10/1998 | Fernandez et al. |
| 5,831,016 A | 11/1998 | Wang et al. |
| 5,844,075 A | 12/1998 | Kawakami et al. |
| 5,897,873 A | 4/1999 | Popescu |
| 5,910,306 A | 6/1999 | Alving et al. |
| 5,919,480 A | 7/1999 | Kedar et al. |
| 5,980,898 A | 11/1999 | Glenn et al. |
| 5,990,287 A | 11/1999 | Hosokawa et al. |
| 6,037,135 A | 3/2000 | Kubo et al. |

(Continued)

FOREIGN PATENT DOCUMENTS

| CA | 2137363 | 6/1999 |
| CA | 2086094 | 5/2000 |

(Continued)

OTHER PUBLICATIONS

Adam et al., "Immune Responses in Cancer," *Pharmacol. Ther.* 99:113-132 (2003).
Alexander et al., "Development of High Potency Universal DR-restricted Helper Epitopes by Modification of High Affinity DR-blocking Peptides," *Immunity* 1:751-761 (1994).
Allegra et al., "Cytotoxins and Cancer Immunotherapy: The Dance of the Macabre?" *J. Nat. Cancer Inst.* 97:1396-1397 (2005).
Antonia et al., "Combination of p53 Cancer Vaccine with Chemotherapy in Patients with Extensive Stage Small Cell Lung Cancer," *Clin. Cancer Res.* 12:878-887 (2006).
"Assessment and Harmonization of Laboratory Diagnostic Procedures Related to Human Papillomavirus Caccine Research and Development," *Technical Meeting: Department of Vaccines and Biologicals*, Heidelberg (2001).
Bagavant et al., "Antifertility Effects of Porcine Zona Pellucida-3 Immunization Using Permissible Adjuvants in Female Bonnet Monkeys (*Macaca radiata*): Reversibility, Effect on Follicular Development and Hormonal Profiles," *J. Reprod. Fertil.* 102:17-25 (1994).

(Continued)

Primary Examiner — Agnieszka Boesen
(74) Attorney, Agent, or Firm — Troutman Sanders LLP

(57) ABSTRACT

The invention compositions comprising a continuous hydrophobic phase and liposomes as a vehicle for delivery of an antigen capable of inducing a cytotoxic T lymphocyte (CTL) response and methods for their use in the treatment of cancer.

6 Claims, 20 Drawing Sheets

(56) References Cited

U.S. PATENT DOCUMENTS

| | | | |
|---|---|---|---|
| 6,090,406 A | 7/2000 | Popescu et al. | |
| 6,093,406 A | 7/2000 | Alving et al. | |
| 6,096,313 A | 8/2000 | Jäger et al. | |
| 6,110,492 A | 8/2000 | Alving et al. | |
| 6,168,804 B1 | 1/2001 | Samuel et al. | |
| 6,183,746 B1 | 2/2001 | Urban et al. | |
| 6,218,371 B1 | 4/2001 | Krieg et al. | |
| RE37,224 E | 6/2001 | Brown et al. | |
| 6,291,430 B1 | 9/2001 | Chaux et al. | |
| 6,309,569 B1 | 10/2001 | Farrar et al. | |
| 6,406,719 B1 | 6/2002 | Farrar et al. | |
| 6,464,980 B1 | 10/2002 | Fikes et al. | |
| 6,472,375 B1 | 10/2002 | Hoon et al. | |
| 6,511,676 B1 | 1/2003 | Boulikas | |
| 6,534,064 B1 | 3/2003 | O'Hagan et al. | |
| 6,537,966 B1 | 3/2003 | Duan et al. | |
| 6,565,777 B2 | 5/2003 | Farrar et al. | |
| 6,588,671 B2 | 7/2003 | King et al. | |
| 6,602,510 B1 | 8/2003 | Fikes et al. | |
| 6,632,447 B1 | 10/2003 | Steiner et al. | |
| 6,670,195 B1 | 12/2003 | Ghiso et al. | |
| 6,793,923 B2 * | 9/2004 | Brown | A61K 9/127 424/184.1 |
| 6,881,405 B2 | 4/2005 | Leveugle et al. | |
| 6,977,074 B2 | 12/2005 | Kündig et al. | |
| 7,019,112 B1 | 3/2006 | Slingluff et al. | |
| 7,026,443 B1 | 4/2006 | Sette et al. | |
| 7,037,509 B2 | 5/2006 | Koelle et al. | |
| 7,056,515 B2 | 6/2006 | Brown et al. | |
| 7,067,120 B2 | 6/2006 | Dianwen et al. | |
| 7,824,686 B2 | 11/2010 | Brown et al. | |
| 2002/0110568 A1 | 8/2002 | Brown et al. | |
| 2003/0044454 A1 | 3/2003 | Fukui et al. | |
| 2003/0185879 A1 | 10/2003 | Boulikas | |
| 2005/0019339 A1 | 1/2005 | Brown et al. | |
| 2005/0037061 A1 | 2/2005 | Hosokawa et al. | |
| 2005/0049197 A1* | 3/2005 | Sette | A61K 39/385 424/192.1 |
| 2005/0079208 A1 | 4/2005 | Albani | |
| 2005/0084524 A1 | 4/2005 | Martin et al. | |
| 2005/0118154 A1 | 6/2005 | Hung et al. | |
| 2005/0158375 A1 | 7/2005 | Kimura et al. | |
| 2005/0202078 A1 | 9/2005 | Schiffelers et al. | |
| 2005/0220781 A1 | 10/2005 | Yan et al. | |
| 2005/0249795 A1 | 11/2005 | Zhang et al. | |
| 2005/0260643 A1 | 11/2005 | Hung et al. | |
| 2006/0008909 A1 | 1/2006 | Cullis et al. | |
| 2006/0182792 A1 | 8/2006 | Richardsen et al. | |

FOREIGN PATENT DOCUMENTS

| | | |
|---|---|---|
| CA | 2436348 | 6/2002 |
| CA | 2 523032 | 4/2007 |
| CA | 2542212 | 4/2007 |
| CA | 2533705 | 7/2007 |
| EP | 1 333 858 | 2/2006 |
| JP | 2004-51238 | 4/2004 |
| JP | 2004-525115 | 8/2004 |
| WO | WO 92/00081 | 1/1992 |
| WO | WO 92/10513 | 6/1992 |
| WO | WO 93/25231 | 12/1993 |
| WO | WO 95/31480 | 11/1995 |
| WO | WO 00/37100 | 6/2000 |
| WO | WO 02/38175 | 5/2002 |
| WO | WO 02/070006 A2 | 9/2002 |
| WO | WO 03/066680 | 8/2003 |
| WO | WO 2004/000873 A2 | 12/2003 |
| WO | WO 04/052917 | 6/2004 |
| WO | WO 04/058179 | 7/2004 |
| WO | WO 04/094454 | 11/2004 |
| WO | WO 05/019435 | 3/2005 |
| WO | WO 2005/025614 A2 | 3/2005 |
| WO | WO 2005/072777 A2 | 8/2005 |
| WO | WO 05/089164 | 9/2005 |

OTHER PUBLICATIONS

Bellone et al., "Relevance of the Tumor Antigen in the Validation of Three Vaccination Strategies for Melanoma," *J. Immunol.* 165:2651-2656 (2000).

Bosch et al., "Prevalence of Human Papillomavirus in Cervivcal Cancer: A Worldwide Perspective," *J. Natl. Cancer Inst.* 87:796-802 (1995).

Bronte et al., "Genetic Vaccination with 'Self' Tyrosinase-related Protein 2 Causes Melanoma Eradication But Not Vitiligo," *Cancer Res.* 60:253-258 (2000).

Brown et al., "Evidence for a Long-lasting Single Administration Contraceptive Vaccine in Wild Grey Seals," *J. Reprod. Immunol.* 35:43-51 (1997).

Brown et al., "Temporal Trends in Antibody Production in Captive Grey, Harp and Hooded Seals to a Single Administration Immunocontraceptive Vaccine," *J. Reprod. Immunol.* 35:53-64 (1997).

Cassarino et al., "The Effects of gp100 and Tyrosinase Peptide Vaccinations on Nevi in Melanoma Patients," *J. Cutaneous Path.* 33:335-342 (2006).

Celis et al., "Recognition of Hepatitis B Surface Antigen by Human T Lymphocytes. Proliferative and Cytotoxic Responses to a Major Antigenic Determinant Defined by Synthetic Peptides," *J. Immunol.* 140:1808-1815 (1988).

Chakraborty et al., "External Beam Radiation of Tumors Alters Phenotype of Tumor Cells to Render Them Susceptible to Vaccine-mediated T-cell Killing," *Cancer Res.* 64:4328-4337 (2004).

Chen et al., "Cytotoxic-T-lymphocute Human Papillomavirus Type 16 E5 Peptide with CpG-oligodeoxynucleotide Can Eliminate Tumor Growth in C57BL/6 Mice," *J. Virol.* 78:1333-1343 (2004).

Chikh et al., "Lipsosomal Delivery of CTL Epitopes to Dendritic Cells," *Biosci. Rep.* 22:339-353 (2002).

Chong et al., "Identification of T-and B-cell Epitopes of the S2 and S3 Subunits of Pertussis Toxin by Use of Synthetic Peptides," *Infection and Immunity* 60:4640-4647 (1992).

Conejero-Lara et al., "Thermal Stability of the Three Domains of Streptokinase Studied by Circular Dichroism and Nuclear Magnetic Resonance," *Protein Sci.* 5:2583-2591 (1996).

Copland et al., "Lipid Based Particulate Formulations for the Delivery of Antigen," *Immunol. Cell Biol.* 83:97-105 (2005).

Correale et al., "Fluorouracil-based Chemotherapy Enhances the Antitumor Activity of a Thymidylate Synthase-directed Polyepitopic Peptide Vaccine," *J. Natl. Cancer Inst.* 97:1437-1445 (2005).

Cui et al., "Liposome-Polycation-DNA (LPD) Particle as a Carrier and Adjuvant for Protein-based Vaccines: Therapeutics Effect Against Cervical Cancer," *Cancer Immunol. Immunother.* 54:1180-1190 (2005).

Daftarian et al., "Eradication of Established HPV 16-expressing Tumors by a Single Administration of a Vaccine Composed of a Liposome-encapsulated CTL-T Helper Fusion Peptide in a Water-in-oil Emulsion," *Vaccine* 24:5235-5244 (2006).

Daftarian et al., "Two Distinct Pathways of Immuno-modulation Improve Potency of p53 Immunization in Rejecting Established Tumors," *Cancer Res.* 64:5407-5414 (2004).

Da Silva et al., "Heterologous Boosting Increases Immunogenicity of Chimeric Papillomavirus Virus-like Particle Vaccines," *Vaccine* 21:3219-3227 (2003).

Davis et al., "CpG DNA is a Potent Enhancer of Specific Immunity in Mice Immunized with Recombinant Hepatitis B Surface Antigen," *J. Immunol.* 160:870-876 (1998).

DeLeo, "p53-Based Immunotherapy of Cancer," *Crit. Rev. Immunol.* 18:29-35 (1998).

Demotz et al., "Delineation of Several DR-restricted Tetanus Toxin T Cell Epitopes," *J. Immunol.* 142:394-402 (1989).

Diethelm-Okita et al., "Universal Epitopes for Human CD4+ Cells on Tetanus and Diphtheria Toxins," *J. Infect. Dis.* 181:1001-1009 (2000).

Dockrell and Kinghorn, "Imiquimod and resiquimod as novel immunomodulators," *Journal of Antimicrobial Chemotherapy* 48: 751-755 (2001).

Dudley et al., "Adoptive Transfer of Cloned Melanoma-reactive T Lymphocytes for the Treatment of Patients with Metastatic Mela-

(56) References Cited

OTHER PUBLICATIONS noma," *J. Immunother.* 24:363-373 (2001).
Edelman et al., "Adjuvants," *Intern. Rev. Immunol.* 7:51-66 (1990).
European Search Report for European Patent Application No. EP 06790800.4 (dated Nov. 13, 2008).
Fagerstone et al., "Wildlife Fertility Control," *The Wildlife Society Technical Review*, University of Nebraska, Lincoln, 02-2:1-29 (2002).
Fausch et al., "Human Papillomavirus Can Escape Immune Recognition Through Langerhans Cell Phosphoinositide 3-Kinase Activation," *J. Immunol.* 174:7172-7178 (2005).
Feltkamp et al., "Vaccination with Cytotoxic T Lymphocyte Epitope-containing Peptide Protects Against a Tumor Induced by Human Papillomavirus Type 16-transformed Cells," *Eur. J. Immunol.* 23:2242-2249 (1993).
Fernando et al., "Vaccine-induced Th1-type Responses are Dominant Over Th2-type Responses in the Short Term Whereas Preexisting Th2 Responses are Dominant in the Longer Term," *Scandinavian J. Immunol.* 47:459-465 (1998).
Fraker et al., "Long-Lasting, Single-Dose Immunocontraception of Feral Fallow Deer in British Columbia," *J. Wildl. Manage.* 66:1141-1147 (2002).
Frazer, "Prevention of Cervical Cancer Through Papillomavirus Vaccination," *Nat. Rev. Immunol.* 4:46-54 (2004).
Frézard, "Liposomes: From Biophysics to the Design of Peptide Vaccines," *Brazilian J. Med. Biol. Res.* 32:181-189 (1999).
Gerard et al., "Therapeutic Potential of Protein and Adjuvant Vaccinations on Tumour Growth," *Vaccine* 19:2583-2598 (2001).
Gillison, "Human Papillomavirus-associated Head and Neck Cancer is a Distinct Epidemiologic, Clinical, and Molecular Entity," *Semin. Oncol.* 31:744-754 (2004).
Gorman et al., "Evaluation of a Porcine Zona Pellucida Vaccine for the Immunocontraception of Domestic Kittens (*Felis catus*)," *Theriogenology* 58:135-149 (2002).
Gregoriadis, "Immunological Adjuvants: A Role for Liposomes," *Immunol. Today* 11:89-97 (1990).
Gulley et al., "Combining a Recombinant Cancer Vaccine with Standard Definitive Radiotherapy in Patients with Localized Prostate Cancer," *Clin. Canc. Res.* 11:3353-3362 (2005).
Gupta et al., "Adjuvants—A Balance Between Toxicity and Adjuvanticity," *Vaccine* 11:293-306 (1993).
Gupta et al., "Adjuvants for Human Vaccines-Current Status, Problems and Future Prospects," *Vaccine* 13:1263-1276 (1995).
Harada et al., "Vaccination of Cytotoxic T Lymphocyte-directed Peptides Elicited and Spread Humoral and Th1-type Immune Responses to Prostate-specific Antigen Protein in a Prostate Cancer Patient," *J. Immunother.* 28:368-375 (2005).
Harrenstien et al., "Effects of Porcine Zona Pellucida Immunocontraceptives in Zoo Felids," *J. Zoo Wildl. Med.* 35:271-279 (2004).
Hilbert et al., "Biodegradable Microsperes Containing Influenza A Vaccine: Immune Response in Mice," *Vaccine* 17:1065-1073 (1999).
Itoh et al., "Transcutaneous Immunization with Cytotoxic T-cell Peptide Epitopes Provides Effective Antitumor Immunity in Mice," *J. Immunother.* 28:430-437 (2005).
Ivanova et al., "Contraceptive Potential of Porcine Zona Pellucida in Cats," *Theriogenology* 43:969-981 (1995).
Jentoft et al., "Labeling of Proteins by Reductive Methylation Using Sodium Cyanoborohydride," *J. Biol. Chem.* 254:4359-4365 (1979).
Jerome et al., "Cytotoxic T Lymphocytes Responding to Low Dose TRP2 Antigen are Induced Against B16 Melanoma by Liposome-encapsulated TRP2 Peptide and CpG DNA Adjuvant," *J. Immunother.* 29:294-305 (2006).
Kadowaki et al., "Subsets of Human Dendritic Cell Precursors Express Different Toll-like Receptors and Respond to Different Microbial Antigens," *J. Exp. Med.* 194:863-869 (2001).
Koutsky et al., "A Controlled Trial of a Human Papillomavirus Type 16 Vaccine," *N. Eng. J. Med.* 347:1645-1651 (2002).
Knutson et al., "Immunization of Cancer Patients with a HER-2/ neu, HLA-A2 Peptide, P369-377, Results in Short-lived Peptide-specific Immunity," *Clin. Canc. Res.* 8:1014-1018 (2002).
Levy et al., "Survey of Zona Pellucida Antigens for Immunocontraception of Cats," *Theriogenology* 63:1334-1341 (2005).
Matthews et al., "Immunogenically Fit Subunit Vaccine Components Via Epitope Discovery from Natural Peptide Libraries," *J. Immunol.* 169:837-846 (2002).
Mayordomo et al., "Bone Marrow-derived Dendritic Cells Pulsed with Synthetic Tumour Peptides Elicit Protective and Therapeutic Antitumour Immunity," *Nat. Med.* 1:1297-1302 (1995).
Millan et al., "CpG DNA Can Induce Strong Th1 Humoral and Cell-mediated Immune Responses Against Hepatitis B Surface Antigen in Young Mice," *Proc. Natl. Acad. Sci.* 95:15553-15558 (1998).
Mosmann, "Role of a New Cytokine, Interleukin-10, in the Cross-Regulation of T Helper Cells," *Acad. Sci.* 628:337-344 (1991).
Muderhwa et al., "Oil-in-water Liposomal Emulsions: Characterization and Potential Use in Vaccine Delivery," *J. Pharm. Sci.* 88:1332-1339 (1999).
Muttilainen et al., "The *Neisseria meningitidis* Outer Membrane Protein P1 Produced in *Baccilus subtilis* and Reconstructed into Phospholipid Vesicles Elicits Antibodies to Native P1 Epitopes," *Microbial Pathogenesis* 18:423-436 (1995).
Nash et al., "Formulation of a Potential Antipregnancy Vaccine Based on the β-subunit of Human Chorionic Gonadotropin (β-hCG). II. Use of Compounds of the Muramyl Dipeptide (MDP) Family as Adjuvants," *J. Reprod. Immunol.* 7:151-162 (1985).
Öhlschläger et al., "Human Papillomavirus Type 16 L1 Capsomeres Induce L1-Specific Cytotoxic T Lymphocytes and Tumor Regression in C57BL/6 Mice," *J. Virol.* 77:4635-4645 (2003).
Padilla-Paz, "Human Papillomavirus Vaccine: History, Immunology, Current Status, and Future Prospects," Clin. *Obstet. Gynecol.* 48:226-240 (2005).
Parkin et al., "Estimating the World Cancer Burden: Globocan 2000," *Int. J. Cancer* 94:153-156 (2001).
Parrado et al., "The Domain Organization of Streptokinase: Nuclear Magnetic Resonance, Circular Dichroism, and Functional Characterization of Proteolytic Fragments," *Protein Sci.* 5:693-704 (1996).
Pilon-Thomas et al., "Immunostimulatory Effects of CpG-ODN Upon Dendritic Cell-Based Immunotherapy in a Murine Melanoma Model," *J. Immunother.* 29:381-387 (2006).
"Porcine Zona Pellucida Immunocontraception in Mammals," The National Wildlife Research Center web site, www.a-phis.usda.gov/ws/nwrc/pzp.htm.
Pye et al., "Selection of an Adjuvant for Vaccination with the Malaria Antigen, MSA-2," *Vaccine* 15:1017-1023 (1997).
Rao et al., "Delivery of Lipids and Liosomal Proteins to the Cytoplasm and Golgi of Antigen-presenting Cells," *Adv. Drug Deliv. Rev.* 41:171-188 (2000).
Rao et al., "Intracellular Processing of Liosome-encapsulated Antigens by Macrophages Depends Upon the Antigen," *Infect. Immun.* 63:2396-2402 (1995).
Rechtsteiner et al., "Cutting Edge: Priming of CTL by transcutaneous peptide immunization with imiquimod," *Journal of Immunology* 174: 2476-2480 (2005).
Reis E Sousa, "Toll-like Receptors and Dendritic Cells: For Whom the Bug Tolls," *Semin. Immunol.* 16:27-34 (2004).
Richards et al., "Liposome-stabilized Oil-in-Water Emulsions as Adjuvants: Increased Emulsion Stability Promotes Induction of Cytotoxic T Lymphocytes Against an HIV Envelope Antigen," *Immunol. Cell Biol.* 82:531-538 (2004).
Sacco et al., "Effect of Varying Dosages and Adjuvants on Antibody Response in Squirrel Monkeys (*Saimiri sciureus*) Immunized with the Porcine Zona Pellucida $M_r$=55,000 Glycoprotein (ZP3)," *Am. J. Reprod. Immunol.* 21:1-8 (1989).
Schreckenberger et al., "Vaccination Strategies for the Treatment and Prevention of Cervical Cancer," *Curr. Opin. Oncol.* 16:485-491 (2004).
Schueler-Furman et al., "Knowledge-Based Structure Prediciton of MHC Class I Bound Peptides: A Study of 23 Complexes," *Folding & Design* 3:549-564 (1998).

(56) References Cited

OTHER PUBLICATIONS

Shedlock et al., "Requirement for CD4 T Cell Help in Generating Functional CD8 T Cell Memory," *Science* 300:337-339 (2003).
Siskind et al., "Cell Selection by Antigen in the Immune Response," *Adv. Immunol.* 10:1-50 (1969).
Smith et al., "In Vivo Generated Th1 Cells Can Migrate to B Cell Follicles to Support B Cell Responses," *J. Immunol.* 173:1640-1646 (2004).
Sparwasser et al., "Bacterial DNA and Immunostimulatory CpG Oligonucleotides Trigger Maturation and Activation of Murine Dendritic Cells," *Eur. J. Immunol.* 28:2045-2054 (1998).
Stern, "Immune Control of Human Papillomavirus (HPV) Associated Anogenital Disease and Potential for Vaccination," *J. Clin. Virol.* 32 Suppl. 1:S72-81 (2005).
Takeuchi et al., "Cutting Edge: Role of Toll-like Receptor 1 in Mediating Immune Response to Microbial Lipoproteins," *J. Immunol.* 169:10-14 (2002).
Teuten et al., "Characterization of Structural and Folding Properties of Streptokinase by N.M.R. Spectroscopy," *Biochem. J.* 290:313-319 (1993).
Tillman et al., "Adenoviral Vectors Targeted to CD40 Enhance the Efficacy of Dendritic Cell-Based Vaccination Against Human Papillomavirus 16-Induced Tumor Cells in a Murine Model," *Cancer Res.* 60:5456-5463 (2000).
Torrens et al., "A Mutant Streptokinase Lacking the C-Terminal 42 Amino Acids is Less Immunogenic," *Immunol. Lett.* 70:213-218 (1999).
Torrens et al., "Immunotherapy with CTL Peptide and VSSP Eradicated Established Human Papillomavirus (HPV) Type 16 E7-Expressing Tumors," *Vaccine* 23:5768-5774 (2005).
Tsukui et al., "Interleukin 2 Production in Vitro by Peripheral Lymphocytes in Response to Human Papillomavirus-Derived Peptides: Correlation with Cervical Pathology," *Cancer Res.* 56:3967-3974 (1996).
Van Oosterhout et al., "Th1/Th2 Paradigm: Not Seeing the Forest for the Trees?" *Eur. Respir. J.* 25:591-593 (2005).
Velders et al., "Eradication of Established Tumors by Vaccination with Venezuelan Equine Encephalitis Virus Replicon Particles Delivering Human Papillomavirus 16 E7 RNA," *Cancer Res.* 61:7861-7867 (2001).
Vierboom et al., "p53: A Target for T-Cell Mediated Immunotherapy," Peptide-Based Cancer Vaccines, W.M. Kast, Ed. Landes Bioscience, Georgetown, pp. 40-55 (2000).
Walboomers et al., "Human Papillomavirus Is a Necessary Cause of Invasive Cervical Cancer Worldwide," *J. Pathol.* 189:12-19 (1999).
Wang et al., "Cutting Edge: CD4+ T Cell Help Can be Essential for Primary CD8+ T Cell Responses in Vivo," *J. Immunol.* 171:6339-6343 (2003).
Weeratna et al., "CpG DNA Induces Stronger Immune Responses with Less Toxicity than Other Adjuvants," *Vaccine* 18:1755-1762 (2000).
Wilcox et al., "Provision of Antigen and CD137 Signaling Breaks Immunological Ignorance, Promoting Regression of Poorly Immunogenic Tumors," *J. Clin. Invest.* 109:651-659 (2002).
Willard et al., "Pregnancy Detection and the Effects of Age, Body Weight, and Previous Reproductive Performance on Pregnancy Status and Weaning Rates of Farmed Fallow Deer (*Dama dama*)," *J. Animal Sci.* 77:32-38 (1999).
Witt et al., "Phase I trial of an oral immunomodulator and interferon inducer in cancer patients," Cancer Research 53: 5176-5180 (1993).
Zinkernagel, "On Cross-priming of MHC Class I-Specific CTL: Rule or Exception?," *Eur. J. Immunol.* 32:2385-2392 (2002).
Zur Hausen, "Papillomavirus and Cancer: From Basic Studies to Clinical Application," *Nat. Rev. Cancer* 2:342-350 (2002).
International Search Report for PCT/CA2006/001640 (dated Jan. 29, 2007).
Office Action for European Patent Application No. 06 790 800.4, dated Oct. 19, 2009.
English Language Summary of an Office Action for Japanese Patent Application No. 2008-533836, dated Sep. 11, 2012 (2 pages).
Office Action for Japanese Patent Application No. 2008-533836, dated Sep. 11, 2012 (6 pages).
Office Action for U.S. Appl. No. 12/992,512, dated Oct. 18, 2012 (14 pages).
Office Action for U.S. Appl. No. 12/679,875, dated Nov. 20, 2012 (11 pages).
Ninomiya et al, "Intranasal administration of a synthetic peptide vaccine encapsulated in liposome together with an anti-CD40 antibody induces protective immunity against influenza A virus in mice," Vaccine. 20(25-26) : 3123-9 (2002).
Final Office Action for U.S. Appl. No. 12/083,209, dated Oct. 27, 2015 (8 pages).

* cited by examiner

USE OF LIPOSOMES IN A CARRIER COMPRISING A CONTINUOUS HYDROPHOBIC PHASE AS A VEHICLE FOR CANCER TREATMENT

CROSS-REFERENCE TO RELATED APPLICATIONS

This application claims the benefit of and priority from Canadian Patent Application Nos. 2,523,032; 2,533,705; and 2,542,212 filed Oct. 7, 2005; Jan. 13, 2006 and Apr. 7, 2006, respectively, and further claims the benefit and priority from U.S. Provisional Patent Application No. 60/806,573, filed Jul. 5, 2006, all of which are incorporated by reference herein.

FIELD OF THE INVENTION

The present application relates to the use of a composition comprising liposomes and a continuous hydrophobic phase as a vehicle for delivery of an antigen capable of inducing a cytotoxic T lymphocyte (CTL) response in the treatment of cancer.

BACKGROUND OF THE INVENTION

Long lasting vaccines comprising liposomes and a variety of antigens have been previously described in the art. These vaccine compositions have been shown to be effective in inducing an enhanced humoral immune response (determined by increased antibody production) against a specific antigen, which is dependent on T helper 2 (Th2) function. However, for a composition to adversely affect cancer, it must be able to induce a cell-mediated (cytotoxic T lymphocyte (CTL)) response. A CTL is a sub-group of T lymphocytes that is capable of inducing the death of infected somatic or tumor cells; they kill (lyse) cells that are infected with viruses (or other pathogens), or are otherwise damaged or dysfunctional. A CTL response is mediated through T helper 1 (Th1) cytokines.

In general, CTL responses are short-lived, lasting only several weeks (Knutson et al., *Clin. Cancer. Res.* 8(5):1014-1018, 1990; Dudley et al., *J. Immunother.* 24(4):363-73, 2002; and Fernando et al., *Scand. J. Immunol.* 47(5):459-65, 1998). Recurrence of cancer is always of concern, thus the induction of a long-lasting CTL response is necessary to ensure that cancers do not reoccur.

Thus, there remains a need for the development of long-lasting immuno-therapeutic compositions for use in the treatment of cancer, without the need for multiple booster treatments.

SUMMARY OF THE INVENTION

In one embodiment, there is provided a composition comprising: a carrier comprising a continuous phase of a hydrophobic substance; liposomes; and at least one antigen capable of inducing a CD8$^+$ cytotoxic T lymphocyte (CTL) response. The composition preferably also comprises at least one T helper epitope.

The present application in a further aspect provides a method for treating cancer in a subject comprising administering the compositions as described herein.

According to another aspect, the present application provides a kit useful for treating cancer in subject comprising a composition as described herein, and instructions for its use thereof.

Other aspects and features of the present invention will become apparent to those of ordinary skill in the art upon review of the following description of specific embodiments of the invention in conjunction with the accompanying figures.

BRIEF DESCRIPTION OF THE FIGURES

In the figures, which illustrate embodiments of the invention by way of example only.

DETAILED DESCRIPTION

Figure 1:
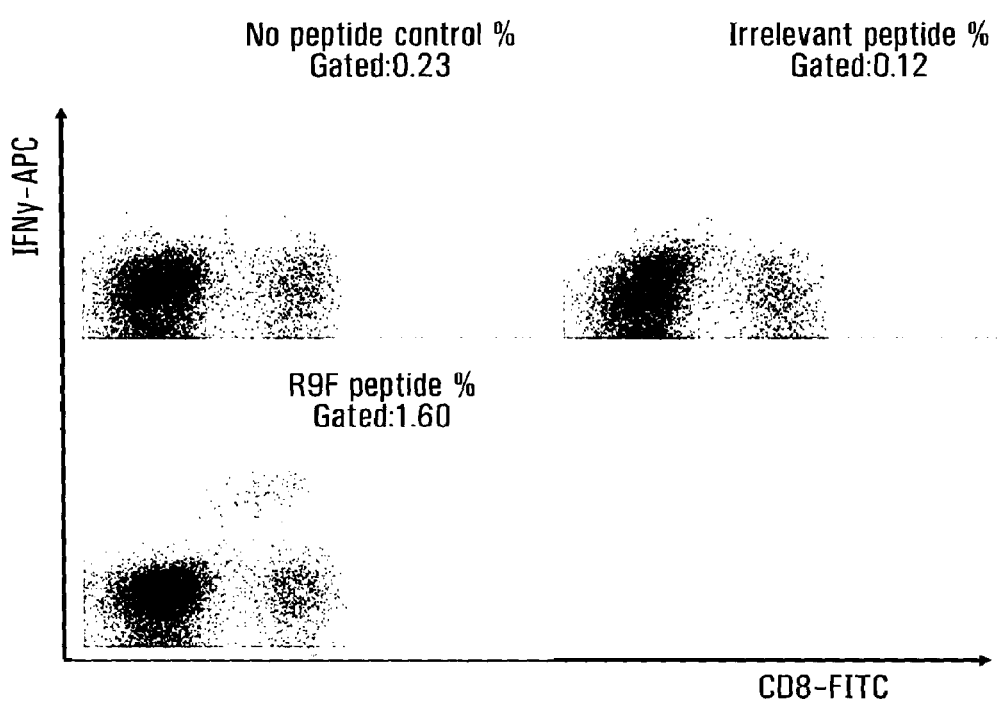
FIG. 1 illustrates ex vivo intracellular IFN-γ staining of splenocytes from mice exposed to an E7 epitope of HPV 16 (R9F peptide; SEQ ID NO: 1), an irrelevant peptide, or no peptide 14 days post-treatment with a composition comprising CpG oligodeoxynucleotide (CpG ODN) (SEQ ID NO: 12), and R9F peptide fused with PADRE encapsulated in liposomes contained in a PBS/FIA water-in-oil emulsion. None of the control treatments caused expansion of CD8+/IFN-γ T cells above background levels when exposed to R9F post-treatment (data not shown). In contrast, a 12.9 fold increase of R9F-responsive CTLs occurred in splenocytes of mice exposed to R9F peptide as compared to mice exposed to irrelevant peptide.

The present application provides compositions comprising at least one antigen capable of inducing a CD8⁺cytotoxic T lymphocyte (CTL) response together with at least one T helper epitope and liposomes suspended in a carrier comprising a continuous phase of a hydrophobic substance. Further, the invention teaches the use of said compositions in a method for treating cancer in a subject.

The compositions as described herein are useful for treating a broad range of cancers, including, without limitation: cancers caused by human papilloma virus (HPV), such as, for example, cervical and/or vulvar cancer; cancers involving expression of tyrosinase, such as, for example, melanoma; cancers involving mutations or overexpression of the p53 gene product, such as, for example, breast cancer or lymph node metastases; and other cancers like melanoma that express more than one tumor-associated protein simultaneously. In another embodiment, the compositions described herein are useful for treating cancers, including, without limitation: lung, ovarian, multiple myeloma, B cell lymphoma, hepatoma, sarcoma, bladder, prostate, thyroid, H/N tumors, colon, rectum, renal, pancreas, gastric, adenocarcinoma, T cell leukemia, lymphosarcoma, uterine, esophageal, non-Hodgkin's lymphomas, endometrial, and RCC tumors. Any cancer that has a cell surface component that is different in quantity or substance from the cell type from which the cancer is derived is a candidate for treatment by the invention. In particular, p53 is a candidate target for broadly applicable cancer treatments (DeLeo, A. B., *Crit. Rev. Immunol.*, 18:29, 1998; Vierboom, M. P. M. et al., *Peptide-Based Cancer Vaccines*. W. M. Kast, ed. Landes Bioscience, Georgetown, 2000).

As used herein, the terms "tumor", "tumor cells", "cancer" and "cancer cells", (used interchangeably) refer to cells that exhibit abnormal growth, characterized by a significant loss of control of cell proliferation or cells that have been immortalized. The term "cancer" or "tumor" includes metastatic as well as non-metastatic cancer or tumors. A cancer may be diagnosed using criteria generally accepted in the art, including the presence of a malignant tumor.

"Treating" or "treatment of" cancer refers to an approach for obtaining beneficial or desired results, including clinical results. Beneficial or desired clinical results can include, but are not limited to, alleviation or amelioration of one or more symptoms or conditions, diminishment of extent of disease, stabilisation of the state of disease, prevention of development of disease, prevention of spread of disease, delay or slowing of disease progression, delay or slowing of disease onset, amelioration or palliation of the disease state, and remission (whether partial or total). "Treating" can also mean prolonging survival of a patient beyond that expected in the absence of treatment. "Treating" can also mean inhibiting the progression of disease temporarily, although more preferably, it involves halting the progression of disease permanently in a subject.

The subject to be treated may be any vertebrate, preferably a mammal, more preferably a human.

Antigens

Suitable antigens of the composition are those that are capable of inducing a cell-mediated (CTL) immune response in a subject.

Cell-mediated immunity is an immune response that does not involve antibodies but rather involves the activation of macrophages and natural killer cells, the production of antigen-specific cytotoxic T lymphocytes and the release of various cytokines in response to an antigen. Cytotoxic T lymphocytes are a sub-group of T lymphocytes (a type of white blood cell) which are capable of inducing the death of infected somatic or tumor cells; they kill cells that are infected with viruses (or other pathogens), or are otherwise damaged or dysfunctional.

Most cytotoxic T cells express T-cell receptors that can recognise a specific peptide antigen bound to Class I MHC molecules. These CTLs also express CD8 (CD8⁺ T cells), which is attracted to portions of the Class I MHC molecule. This affinity keeps the CTL and the target cell bound closely together during antigen-specific activation.

Cellular immunity protects the body by, for example, activating antigen-specific cytotoxic T-lymphocytes that are able to lyse body cells displaying epitopes of foreign antigen on their surface, such as virus-infected cells, cells with intracellular bacteria, and cancer cells displaying tumor antigens; activating macrophages and natural killer cells, enabling them to destroy intracellular pathogens; and stimulating cells to secrete a variety of cytokines that influence the function of other cells involved in adaptive immune responses and innate immune responses.

In one embodiment, the antigen may be, for example, a peptide, a suitable native, non-native, recombinant or denatured protein or polypeptide, or a fragment thereof, or an epitope that is capable of producing a CTL immune response in a subject.

The term "polypeptide" encompasses any chain of amino acids, regardless of length (e.g., at least 6, 8, 10, 12, 14, 16, 18, or 20 amino acids) or post-translational modification (e.g., glycosylation or phosphorylation), and includes, for example, natural proteins, synthetic or recombinant polypeptides and peptides, epitopes, hybrid molecules, variants, homologs, analogs, peptoids, peptidomimetics, etc. A variant or derivative therefore includes deletions, including truncations and fragments; insertions and additions, for example conservative substitutions, site-directed mutants and allelic variants; and modifications, including peptoids having one or more non-amino acyl groups (for example, sugar, lipid, etc.) covalently linked to the peptide and post-translational modifications. As used herein, the term "conserved amino acid substitutions" or "conservative substitutions" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

Polypeptides, peptides or epitopes that have substantial identity to those disclosed herein may be used. Two sequences are considered to have substantial identity if, when optimally aligned (with gaps permitted), they share at least approximately 50% sequence identity, or if the sequences share defined functional motifs. In alternative embodiments, optimally aligned sequences may be considered to be substantially identical (i.e., to have substantial identity) if they share at least 60%, 70%, 75%, 80%, 85%, 90%, 95%, 96%, 97%, 98%, 99% identity over a specified region. The term "identity" refers to sequence similarity between two polypeptides molecules. Identity can be determined by comparing each position in the aligned sequences. A degree of identity between amino acid sequences is a function of the number of identical or matching amino acids at positions shared by the sequences, for example, over a specified region. Optimal alignment of sequences for comparisons of identity may be conducted using a variety of algorithms, as are known in the art, including the ClustalW program, available at http://clustalw.genome.ad.jp, the local homology algorithm of Smith and Waterman, 1981, Adv. Appl. Math 2: 482, the homology alignment algorithm of Needleman and Wunsch, 1970, J. Mol. Biol. 48:443, the search for similarity method of Pearson and Lipman, 1988, Proc. Natl. Acad. Sci. USA 85:2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, J. Mol. Biol. 215:403-10 (using the published default settings). Software for performing BLAST analysis is available through the National Center for Biotechnology Information (through the internet at http://www.ncbi.nlm.nih.gov/).

The amount of antigen used in a single treatment with a composition as described herein may vary depending on the type of antigen and the size of the subject. One skilled in the art will be able to determine, without undue experimentation, the effective amount of antigen to use in a particular application. The term "effective amount" as used herein means an amount effective, at dosages and for periods of time necessary, to achieve the desired result.

In one embodiment, the antigen may be at least one CTL epitope capable of inducing a CTL response. For example, the antigen may be a CTL epitope derived from a virus, such as HPV.

In another embodiment, the antigen may be a CTL epitope selected from the group consisting of an epitope derived from the E6 or E7 protein of HPV.

In a further embodiment, the epitope of E6 protein of HPV comprises the peptide sequence TIHDIILECV (T10V) (SEQ ID NO: 5). In another embodiment, the epitope of the E7 protein of HPV comprises a peptide sequence selected from the group consisting of RAHYNIVTF (R9F) (SEQ ID NO: 1), YMLDLQPETT (Y10T) (SEQ ID NO: 2), LLMGTLGIV (L9V) (SEQ ID NO: 3), and TLGIVCPI (T81) (SEQ ID NO: 4).

In another embodiment, the CTL epitope may be an epitope of a tumor-associated protein, such as for example, a melanoma-associated protein. In a further embodiment, the melanoma-associated protein is a tyrosine related protein-2 (TRP-2) or p53, which can be obtained by various methods including recombinant technology or chemical synthesis.

In one embodiment an epitope of a TRP-2 derived protein comprises the peptide sequence, for example, SVYDFFVWL (S9L; SEQ ID NO: 7). In another embodiment, an epitope of a TRP-2 derived protein comprises the peptide sequence VYDFFVWL (V8L; SEQ ID NO: 6). In another embodiment, an epitope of a p53 derived protein comprises a peptide sequence selected from KYMCNSSCM (K9M; wild type p53; SEQ ID NO: 9), KYICNSSCM (mK9M; modified p53; SEQ ID NO: 8), and AKXVAAWTL-KAAAKYICNSSCM (mK9M (SEQ ID NO: 9) coupled to PADRE (SEQ ID NO: 10)).

In one embodiment, the composition may comprise a mixture of CTL epitopes as antigens for inducing a CTL response.

In a further embodiment, the antigen may be any peptide or polypeptide that is capable of inducing a specific CTL response that is able to effectively recognise a specific conformation on targeted tumor cells and cause their destruction.

In still a further embodiment, the antigen may comprise a peptide sequence selected from the following table:

TABLE 1

| Antigen | Sequence | HLA | Patent |
| --- | --- | --- | --- |
| Mart-1/ Melan-A | AAGIGILTV (SEQ ID NO: 18) | A2 | U.S. Pat. No. 5,844,075 |
|  | EAAGIGILTV (SEQ ID NO: 19) | A2 | U.S. Pat. No. 5,844,075 |
|  | ILTVILGVL (SEQ ID NO: 20) | A2 | U.S. Pat. No. 5,844,075 |
|  | AEEAAGIGIL (SEQ ID NO: 21) | B45 | U.S. Pat. No. 7,037,509 |

TABLE 1-continued

| Antigen | Sequence | HLA | Patent |
|---|---|---|---|
| | AEEAAGIGILT (SEQ ID NO: 22) | B45 | Unknown |
| MC1R | TILLGIFFL (SEQ ID NO: 23) | A2 | Unknown |
| | FLALIICNA (SEQ ID NO: 24) | A2 | Unknown |
| Gp100 | KTWGQYWQV (SEQ ID NO: 25) | A2 | U.S. Pat. No. 5,844,075 |
| Gp100 | AMLGTHTMEV (SEQ ID NO: 26) | A2 | Unknown |
| | MLGTHTMEV (SEQ ID NO: 27) | A2 | Unknown |
| | SLADTNSLAV (SEQ ID NO: 28) | A2 | U.S. Pat. No. 5,844,075 |
| | ITDQVPFSV (SEQ ID NO: 29) | A2 | U.S. Pat. No. 5,844,075 |
| | LLDGTATLRL (SEQ ID NO: 30) | A2 | U.S. Pat. No. 5,844,075 |
| | YLEPGPVTA (SEQ ID NO: 31) | A2 | U.S. Pat. No. 5,844,075 |
| | VLYRYGSFSV (SEQ ID NO: 32) | A2 | U.S. Pat. No. 5,844,075 |
| | RLPRIFCSC (SEQ ID NO: 33) | A2 | Unknown |
| | LIYRRRLMK (SEQ ID NO: 34) | A3 | Unknown |
| | ALNFPGSQK (SEQ ID NO: 35) | A3 | Unknown |
| | SLIYRRRLMK (SEQ ID NO: 36) | A3 | Unknown |
| | ALLAVGATK (SEQ ID NO: 37) | A3 | U.S. Pat. No. 6,558,671 |
| | ALLAVGATK (SEQ ID NO: 38) | A3 | U.S. Pat. No. 6,977,074 |
| | VYFFLPDHL (SEQ ID NO: 39) | A24 | Unknown |
| | SNDGPTLI (SEQ ID NO: 40) | Cw8 | Unknown |
| PSA | VSHSFPHPLY (SEQ ID NO: 41) | A1 | U.S. Pat. No. 6,037,135 |
| | FLTPKKLQCV (SEQ ID NO: 42) | A2 | U.S. Pat. No. 6,881,405 |
| | VISNDVCAQV (SEQ ID NO: 43) | A2 | Unknown |
| PSM | HSTNGVTRIY (SEQ ID NO: 44) | A1 | Unknown |
| Tyrosinase | KCDICTDEY (SEQ ID NO: 45) | A1 | U.S. Pat. No. 7,019,112 |
| | SSDYVIPIGTY (SEQ ID NO: 46) | A1 | Unknown |
| Tyrosinase | YMDGTMSQV (SEQ ID NO: 47) | A2 | U.S. Pat. No. 6,096,313 |
| | MLLAVLYCL (SEQ ID NO: 48) | A2 | U.S. Pat. No. 6,291,430 |
| | AFLPWHRLF (SEQ ID NO: 49) | A24 | U.S. Pat. No. 6,291,430 |
| | SEIWRDIDF (SEQ ID NO: 50) | B44 | U.S. Pat. No. 6,291,430 |
| | MSLQRQFLR (SEQ ID NO: 51) | A31 | U.S. Pat. No. 5,831,016 |
| TRP1 | SVYDFFVWL (SEQ ID NO: 52) | A2 | U.S. Pat. No. 7,067,120 |
| TRP2 | TLDSQVMSL (SEQ ID NO: 53) | A2 | Unknown |
| | LLGPGRPYR (SEQ ID NO: 54) | A31 | U.S. Pat. No. 5,831,016 |
| p53 | ANDPIFVVL (SEQ ID NO: 55) | Cw8 | Unknown |

As indicated above in Table 1, proteins (polypeptides) vary in the number of peptide sequences that may serve as CTL-epitopes and consequently can be used in the present invention. The following genes, without limitation, code for tumor-associated proteins that have peptide sequences that can be incorporated as antigens in the invention: p53, HPV E6 and E7, ART-4, CAMEL, CEA, Cyp-B, HER2/neu, hTERT, hTRT, iCE, MUC1, MUC2, PRAME, P15, RU1, RU2, SART-1, SART-3, WT1, PSA, tyrosinase, TRP-1, TRP-2, gp100, MART-1/Melan A, MAGE-A1, MAGE-A2, MAGE-A3, MAGE-A6, MAGE-A10, MAGE-A12, BAGE, DAM-6, DAM-10, GAGE-1, GAGE-2, GAGE-3, GAGE-4, GAGE-5, GAGE-6, GAGE-7B, GAGE-8, NA88-A, NY-ESO-1, NY-ESO-1a (CAG-3), AFP, β-catenin/m, Caspase-8/m, CDK-4/m, ELF2M, GnT-V, G250, Ras, HSP70-2M, HST-2, KIAA0205, MUM-1, MUM-2, MUM-3, Myosin/m, RAGE, SART-2, TRP-2/INT2, and 707-AP.

T Helper Epitopes

T helper epitopes are a sequence of amino acids (natural or non-natural amino acids) that have T helper activity. T helper epitopes are recognised by T helper lymphocytes, which play an important role in establishing and maximising the capabilities of the immune system, and are involved in activating and directing other immune cells, such as cytotoxic T lymphocytes.

A T helper epitope can consist of a continuous or discontinuous epitope. Hence not every amino acid of a T helper is necessarily part of the epitope. Accordingly, T helper epitopes, including analogs and segments of T helper epitopes, are capable of enhancing or stimulating an immune response. Immunodominant T helper epitopes are broadly reactive in animal and human populations with widely divergent MHC types (Celis et al. (1988) *J. Immunol.* 140:1808-1815; Demotz et al. (1989) *J. Immunol.* 142:394-402; Chong et al. (1992) *Infect. Immun.* 60:4640-4647). The T helper domain of the subject peptides has from about 10 to about 50 amino acids and preferably from about 10 to about 30 amino acids. When multiple T helper epitopes are present, then each T-helper epitope acts independently.

In one embodiment, the composition described herein also comprises at least one T helper epitope. In some instances, the T-helper epitope may form part of the antigen. In particular, if the antigen is of sufficient size, it may contain an epitope that functions as a T-helper epitope. In other embodiments, the T-helper epitope is a separate molecule from the antigen.

In another embodiment, T helper epitope analogs may include substitutions, deletions and insertions of from one to about 10 amino acid residues in the T helper epitope. T helper segments are contiguous portions of a T helper epitope that are sufficient to enhance or stimulate an immune response. An example of T-helper segments is a series of overlapping peptides that are derived from a single longer peptide.

Sources of T helper epitopes for use in the present invention include, for example, hepatitis B surface antigen helper T cell epitopes, pertussis toxin helper T cell epitopes, measles virus F protein helper T cell epitope, *Chlamydia trachomitis* major outer membrane protein helper T cell epitope, diphtheria toxin helper T cell epitopes, *Plasmodium falciparum* circumsporozoite helper T cell epitopes, *Schistosoma mansoni* triose phosphate isomerase helper T cell epitopes, *Escherichia coli* TraT helper T cell epitopes and immune-enhancing analogs and segments of any of these T helper epitopes.

In one embodiment, the T helper epitope is a universal T helper epitope. A universal T helper epitope as used herein refers to a peptide or other immunogenic molecule, or a fragment thereof, that binds to a multiplicity of MHC class II molecules in a manner that activates T-cell function in a class II (CD4+ T cells) or class I (CD8+ T cells)-restricted manner.

In another embodiment, the T helper epitope may be a universal T helper epitope such as PADRE (pan-DR epitope) comprising the peptide sequence AKXVAAWTLKAAA (SEQ ID NO: 10), wherein X may be cyclohexylalanyl. PADRE specifically has a CD4+ T-helper epitope, that is, it stimulates induction of a PADRE-specific CD4+ T helper response.

Tetanus toxoid has T helper epitopes that work in the similar manner as PADRE. Tetanus and diphtheria toxins have universal epitopes for human CD4+ cells. (Diethelm-Okita, B. M. et al., Universal epitopes for human CD4+ cells on tetanus and diphtheria toxins. *J. Infect. Diseases*, 181: 1001-1009, 2000). In another embodiment, the T helper epitope may be a tetanus toxoid peptide such as F21E comprising the peptide sequence FNNFTVSFWLRVPK-VSASHLE (amino acids 947-967; SEQ ID NO: 11).

In another embodiment, the T helper epitope is fused to at least one antigen (i.e., a peptide), or a mixture of antigens, to make a fusion peptide.

Carriers

The carrier of the composition comprises a continuous phase of a hydrophobic substance, preferably a liquid hydrophobic substance. The continuous phase may be an essentially pure hydrophobic substance or a mixture of hydrophobic substances. In addition, the carrier may be an emulsion of water in a hydrophobic substance or an emulsion of water in a mixture of hydrophobic substances, provided the hydrophobic substance constitutes the continuous phase. Further, in another embodiment, the carrier may function as an adjuvant.

Hydrophobic substances that are useful in the compositions as described herein are those that are pharmaceutically and/or immunologically acceptable. The carrier is preferably a liquid but certain hydrophobic substances that are not liquids at atmospheric temperature may be liquefied, for example by warming, and are also useful in this invention. In one embodiment, the hydrophobic carrier may be a PBS/FIA emulsion.

Oil or water-in-oil emulsions are particularly suitable carriers for use in the present invention. Oils should be pharmaceutically and/or immunologically acceptable. Preferred examples of oils are mineral oil (especially light or low viscosity mineral oil), vegetable oil (e.g., corn or canola oil), nut oil (e.g., peanut oil) and squalene. A low viscosity mineral oil is most preferred. Animal fats and artificial hydrophobic polymeric materials, particularly those that are liquid at atmospheric temperature or that can be liquefied relatively easily, may also be used.

Liposomes

Liposomes are completely closed lipid bilayer membranes containing an entrapped aqueous volume. Liposomes may be unilamellar vesicles (possessing a single bilayer membrane) or multilamellar vesicles characterized by multimembrane bilayers, each bilayer may or may not be separated from the next by an aqueous layer. A general discussion of liposomes can be found in Gregoriadis G. *Immunol. Today*, 11:89-97, 1990; and Frezard, F., *Braz. J. Med. Bio. Res.*, 32:181-189, 1999.

Although any liposomes may be used in this invention, including liposomes made from archaebacterial lipids, particularly useful liposomes use phospholipids and unesterified cholesterol in the liposome formulation. The cholesterol is used to stabilize the liposomes and any other compound that stabilizes liposomes may replace the cholesterol. Other liposome stabilizing compounds are known to those skilled in the art. For example, saturated phospholipids produce liposomes with higher transition temperatures indicating increased stability. To avoid limiting the electrostatic association between the antigen and the liposomes, the antigen may be sequestered in the interior of the liposomes.

Phospholipids that are preferably used in the preparation of liposomes are those with at least one head group selected from the group consisting of phosphoglycerol, phosphoethanolamine, phosphoserine, phosphocholine and phosphoinositol. More preferred are liposomes that comprise lipids in phospholipon 90 G. When unesterified cholesterol is also used in liposome formulation, the cholesterol is used in an amount equivalent to about 10% of the amount of phospholipid. If a compound other than cholesterol is used to stabilize the liposomes, one skilled in the art can readily determine the amount needed in the composition.

Liposome compositions may be obtained, for example, by using natural lipids, synthetic lipids, sphingolipids, ether lipids, sterols, cardiolipin, cationic lipids and lipids modified with poly (ethylene glycol) and other polymers. Synthetic lipids may include the following fatty acid constituents; lauroyl, myristoyl, palmitoyl, stearoyl, arachidoyl, oleoyl, linoleoyl, erucoyl, or combinations of these fatty acids.

Adjuvants

The composition may further comprise one or more pharmaceutically acceptable adjuvants, excipients, etc., as are known in the art. See, for example, Remington's Pharmaceutical Sciences (Remington's Pharmaceutical Sciences, Mack Publishing Company, Easton, Pa., USA 1985) and The United States Pharmacopoeia: The National Formulary (USP 24 NF19) published in 1999. In one embodiment, suitable adjuvants include a CpG-containing oligodeoxynucleotide (CpG ODN). For example,

5'-TCCAT<u>GACGTT</u>CCT<u>GACGTT</u>- 3'.

The skilled person may select an appropriate CpG on the basis of the target species and efficacy. In place of CpG, a lipopeptide, such as Pam3Cys-SKKK)(EMC Microcollections, Germany) or variants, homologs and analogs thereof may be used. In this regard, the Pam2 family of lipopeptides has been shown to be an effective alternative to the Pam3 family of lipopeptides.

The amount of adjuvant used depends on the amount of antigen and on the type of adjuvant. One skilled in the art can readily determine the amount of adjuvant needed in a particular application.

Compositions

In one embodiment, compositions as described herein may be formulated by encapsulating an antigen (defined as a substance that interacts specifically with free antibody and/or with antigen-binding receptors on lymphocytes) or an antigen/adjuvant complex in liposomes to form a liposome-encapsulated antigen and mixing the liposome-encapsulated antigen with a carrier comprising a continuous phase of a hydrophobic substance. If an antigen/adjuvant complex is not used in the first step, a suitable adjuvant may be added to the liposome-encapsulated antigen, to the mixture of liposome-encapsulated antigen and carrier, or to the carrier before the carrier is mixed with the liposome-encapsulated antigen. The order of the process may depend on the type of adjuvant used. The resulting liposome-encapsulated antigen is then mixed with the carrier. (It should be noted that the term "liposome-encapsulated antigen" may refer to liposome-encapsulation of the antigen alone or to the encapsulation of the antigen/adjuvant complex depending on the context.) This promotes intimate contact between the adjuvant and the antigen and may, at least in part, account for the good immune response. To facilitate use of some adjuvants, the antigen may be first encapsulated in liposomes and the resulting liposome-encapsulated antigen is then mixed with the adjuvant in a carrier comprising a continuous phase of hydrophobic substance.

In formulating a composition that is substantially free of water, the antigen or antigen/adjuvant complex may be encapsulated with liposomes, which may or may not be freeze-dried, and suspended in a hydrophobic substance. In formulating a composition in an emulsion of water in a hydrophobic substance, the antigen or antigen/adjuvant complex may be encapsulated in liposomes, suspended in an aqueous medium followed by the mixing of the aqueous medium with a hydrophobic substance to form an emulsion. In the case of the emulsion, to maintain the hydrophobic substance in the continuous phase, the aqueous medium containing the liposomes may be added in aliquots with mixing to the hydrophobic substance.

In one embodiment, the antigen or the liposome-encapsulated antigen may be freeze-dried before being mixed with the hydrophobic substance or with the aqueous medium as the case may be. In another embodiment, an antigen/adjuvant complex may be encapsulated by liposomes followed by freeze-drying. In a further embodiment, the antigen may be encapsulated in liposomes followed by the addition of adjuvant then freeze-drying to form a freeze-dried liposome-encapsulated antigen with external adjuvant. In yet another instance, the antigen may be encapsulated by liposomes followed by freeze-drying before the addition of adjuvant. Freeze-drying may promote better interaction between the adjuvant and the antigen.

In another embodiment, formulation of the liposome-encapsulated antigen into a hydrophobic substance may also involve the use of an emulsifier to promote more even distribution of the liposomes in the hydrophobic substance. Typical emulsifiers are well-known in the art and include mannide oleate (Arlacel™ A), lecithin, Tween™ 80, and Spans™ 20, 80, 83 and 85. The emulsifier is used in an amount effective to promote even distribution of the liposomes. Typically, the volume ratio (v/v) of hydrophobic substance to emulsifier is in the range of about 5:1 to about 15:1 with a ratio of about 10:1 being preferred.

Alternatively, the antigen or antigen/adjuvant complex may be associated with, in contact with or separate from liposomes and not encapsulated in liposomes. The efficiency of liposome encapsulation of some hydrophilic antigens or hydrophilic antigen/adjuvant complexes may be poor so that upon being placed in a hydrophobic environment or freeze-drying most of the antigen becomes associated with the external surface of the liposomes. This represents another embodiment of the invention.

In a further embodiment, an antigen (peptide or polypeptide) having a CTL epitope and PADRE (fused to the antigen or separate) may be encapsulated together in liposomes. In another embodiment, more than one antigen may be placed together in the same liposomes. In a further embodiment, other substances may be in used instead of PADRE that have a T-helper epitope, for example, tetanus toxoid peptide(s). In a another embodiment, an adjuvant, preferably a CpG-containing ODN, may be encapsulated in the liposomes as well. The liposomes are preferably suspended in PBS. This suspension is then emulsified in a hydrophobic carrier, for example, ISA51 or mineral oil. The result is that liposomes containing the antigen(s) and adjuvant(s), preferably PADRE and CpG) are suspended in PBS which in turn is emulsified in a hydrophobic carrier, for example, ISA51 or mineral oil.

Recurrence of cancer is always of concern, thus the induction of a long-lasting CTL response is important to ensure that cancers do not reoccur. In general, CTL responses are short-lived lasting only several weeks, however, the compositions as described herein are capable of inducing a potent CTL response that lasts for at least 30, 40, 50, 60, 70, 80, 90, 100, 110, 120 or 130 days.

Figure 3:
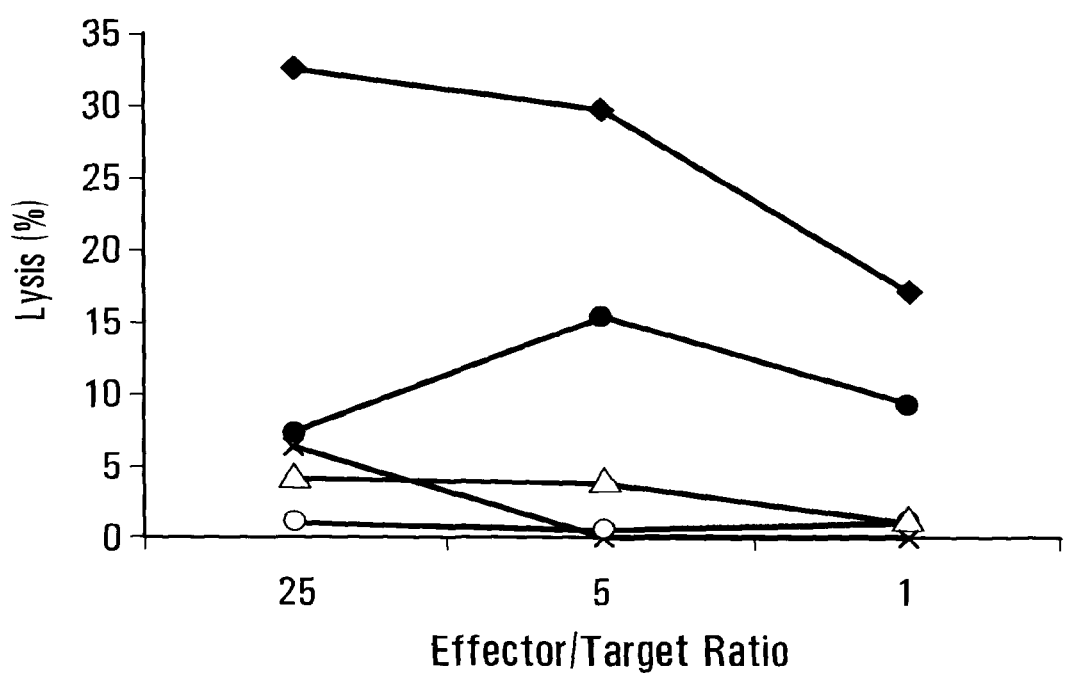
FIG. 3 illustrates lysis of EL-4 cells by splenocytes from mice treated with one of the following compositions: (i) a fusion peptide (R9F peptide (SEQ ID NO: 1) fused with PADRE (SEQ ID NO: 10)) and CpG ODN (SEQ ID NO: 12) encapsulated in liposomes suspended in a PBS/FIA water-in-oil emulsion (diamonds); (ii) unencapsulated fusion peptide and CpG ODN (SEQ ID NO: 12) in a PBS/FIA water-in-oil emulsion (triangles and crosses), or (iii) liposome encapsulated fusion peptide in a PBS/FIA water-in-oil emulsion (closed circles). The splenocytes were then exposed to either R9F peptide (crosses, diamonds and closed circles) or an irrelevant peptide (SEQ ID NO: 13) (triangles and open circles) 130 days post-treatment. Splenocytes from mice treated with fusion peptide alone showed base levels of lysis of EL-4 cells exposed to either R9F or an irrelevant peptide 130 days post-treatment (data not shown).

In one embodiment, splenocytes isolated from mice treated 130 days prior with a composition comprising a CpG ODN and a CTL epitope of E7 protein of HPV fused to PADRE encapsulated in liposomes suspended in a water-in-oil emulsion retained the ability to lyse mouse lymphoma EL-4 cells (FIG. 3). These results indicate that compositions as described herein are able to induce a long-lasting CTL response, which is desirable in cancer treatment.

Figure 6:
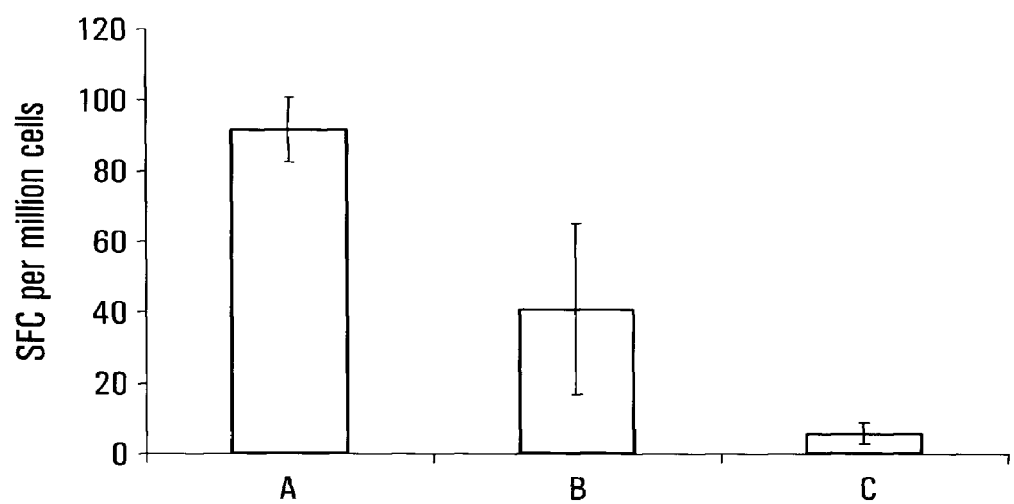
FIG. 6 illustrates ex vivo detection of TRP-2 specific IFN-γ producing splenocytes (spot forming cells, SFC) in mice 8 days following a single treatment with one of the following: (A) a composition comprising a tyrosine-related protein-2 (TRP-2) peptide (S9L; SEQ ID NO: 7) with PADRE (SEQ ID NO: 10) and CpG ODN (SEQ ID NO: 12) encapsulated in liposomes suspended in a PBS/ISA51 water-in-oil emulsion; (B) a composition comprising S9L with PADRE in liposomes suspended in a water-in-oil emulsion; or (C) a composition comprising an irrelevant peptide (SEQ ID NO: 13) with CpG in liposomes suspended in PBS/ISA51 a water-in-oil emulsion.
Figure 7:
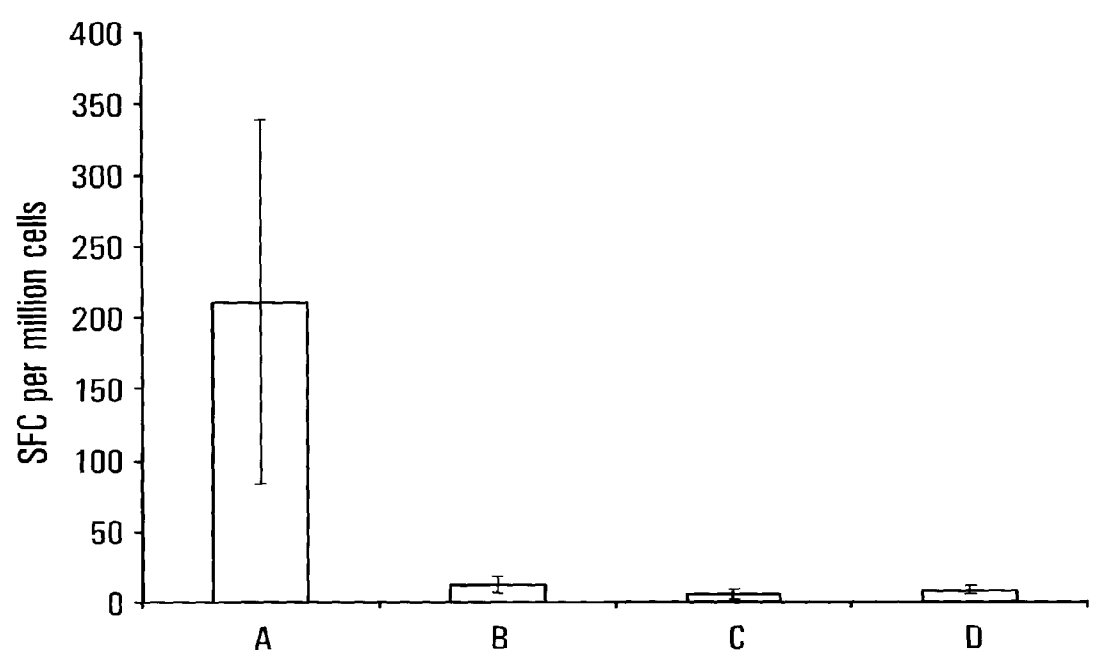
FIG. 7 illustrates ex vivo detection of p53 specific IFN-γ producing splenocytes (SFC) in mice following a single treatment with (A) a modified p53 peptide (mK9M; SEQ ID NO: 8) with PADRE (SEQ ID NO: 10) and CpG ODN (SEQ ID NO: 12) encapsulated in liposomes and suspended in a PBS/ISA51 water-in-oil emulsion, or one of the following control compositions: (B) mK9M with PADRE in a water-in-oil emulsion; (C) mK9M with PADRE encapsulated in liposomes and suspended in a water-in-oil emulsion; and (D) an irrelevant peptide (SEQ ID NO: 13) with CpG ODN encapsulated in liposomes and suspended in a water-in-oil emulsion.
Figure 8:
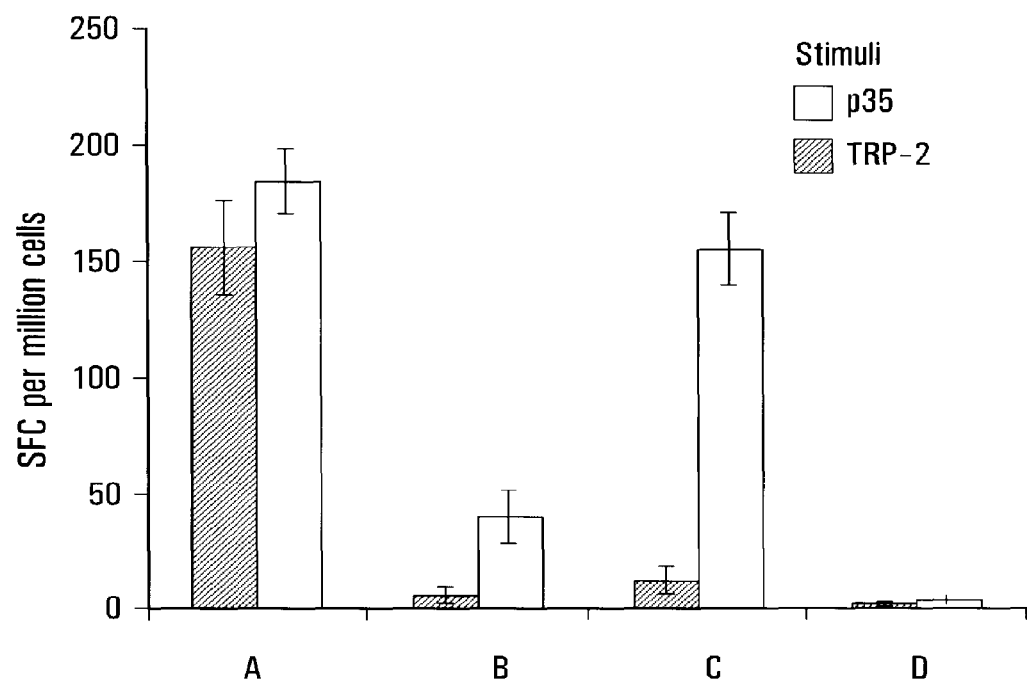
FIG. 8 illustrates ex vivo detection of TRP-2- and p53-specific IFN-γ producing splenocytes (SFC) in mice following a single treatment with a composition comprising (A) p53 (mK9M peptide; SEQ ID NO: 8) and TRP-2 (V8L; SEQ ID NO: 6) peptides with PADRE (SEQ ID NO: 10) and CpG ODN (SEQ ID NO: 12) encapsulated in liposomes and suspended in a PBS/ISA51 water-in-oil emulsion or one of the following control compositions: (B) p53 and TRP-2 peptides with PADRE encapsulated in liposomes and suspended in a PBS/ISA51 water-in-oil emulsion; (C) p53 and TRP-2 peptides with PADRE and CpG ODN; (D) p53 and TRP-2 peptides with PADRE.

In one embodiment, treatment with compositions comprising CpG ODN adjuvant and TRP-2 and/or p53 peptides as antigens were able to increase the number of antigen-specific interferon-gamma (IFN-γ) producing splenocytes needed to combat cancer cells (FIGS. 6-8). Antigens were fused to a universal T helper epitope (PADRE) and encapsulated in liposomes suspended in a water-in-oil emulsion. Both the peptide and tumor cells expressing the protein from which the peptide was derived were able to induce IFN-γ production, demonstrating that use of the composition of invention to deliver peptide antigens resulted in an immune response relevant to the intended target.

In another embodiment, treatment of established tumors with a single treatment with compositions as described herein was effective in significantly reducing tumor size and the percentage of mice with tumors post-treatment (FIGS. 9-13 and 15).

Treatment with compositions as described herein may be followed by a dermal application to the site of administration of a suitable composition comprising imiquimod (1-(2-methylpropyl)-1H-imidazo[4,5-c]quinolin-4-amine) or analogues thereof that are members of a class of non-nucleoside imidazoquinolinamines (hetero-cyclic amine) that activate the immune system through localised induction of cytokines. Imiquimod is a ligand for TLR7 and activates a Th1-like cytokine milieu that includes IFN-α, TNF-α, IL-1α, IL-6, and IL-8. In a further embodiment, treatment with compositions as described herein may be followed by a dermal application to the site of administration of Aldara™ ointment (imiquimod 5%) (3M, St. Paul, Minn., U.S.A.) to the site of treatment administration.

Figure 18:
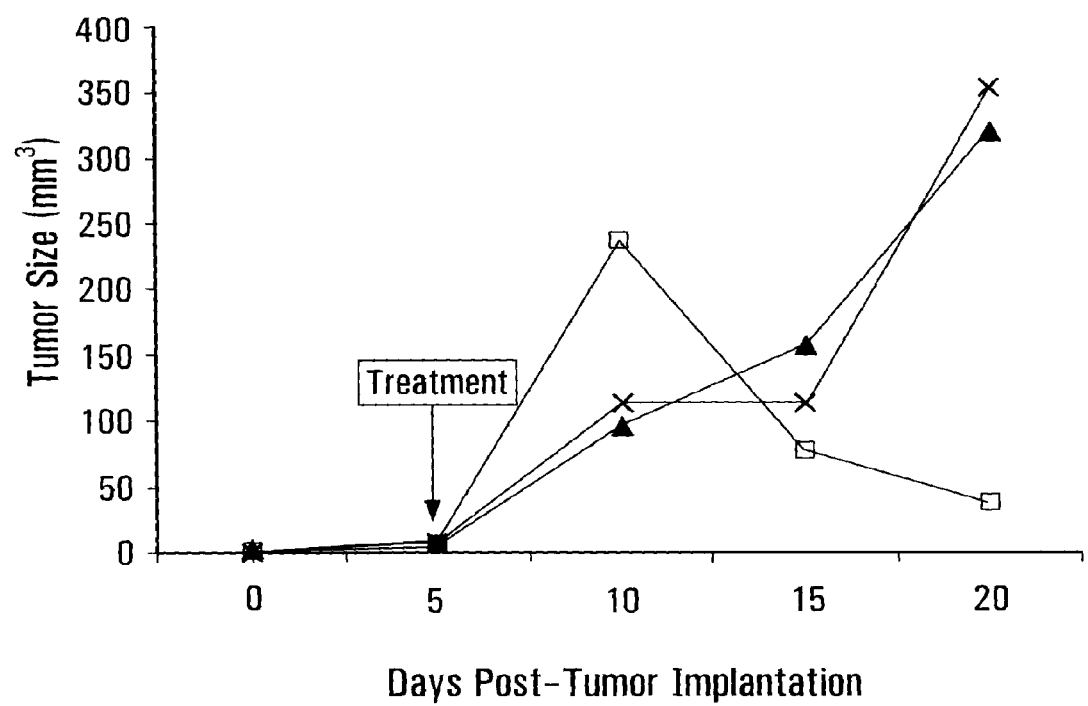
FIG. 18 illustrates that C3 tumors were reduced in size in mice treated with a composition comprising CpG ODN (SEQ ID NO: 12) and an E7 epitope of HPV 16 (R9F peptide; SEQ ID NO: 1) encapsulated in liposomes and suspended in a PBS/ISA51 water-in-oil emulsion, followed by dermal application of Aldara™ within 15-20 hours (squares). In contrast, C3 tumors were not reduced in size in control mice that received PBS (crosses) or PBS followed by dermal application of Aldara within 15-20 hours to the site of PBS injection (triangles). Treatment was administered 5 days post tumor implantation in all treatment groups. Tumor size is the average size of tumors in ten mice.
Figure 19:
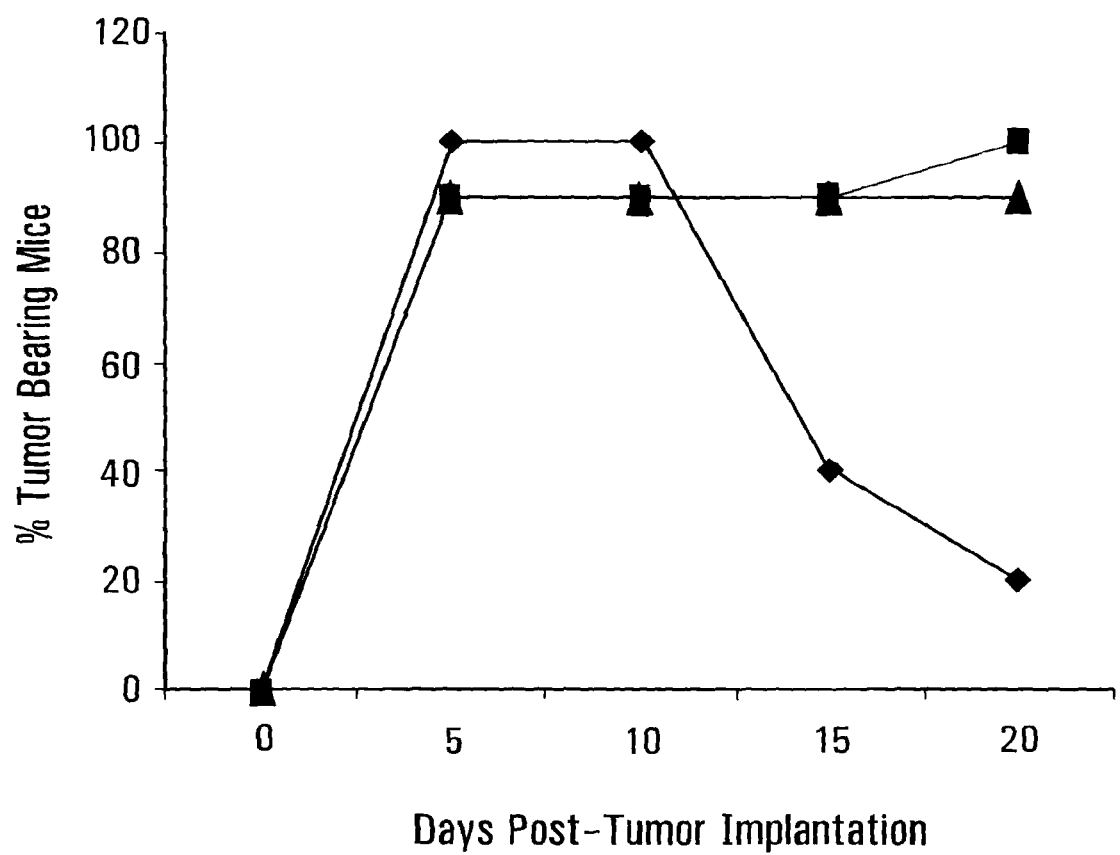
FIG. 19 illustrates the percentage of mice having a palpable tumor after treatment five days post tumor implantation in all treatment groups. Only 20% of mice 20 days post-tumor implantation had a palpable tumor after treatment with a composition comprising CpG ODN (SEQ ID NO: 12) and an E7 epitope of HPV 16 (R9F peptide; SEQ ID NO: 1) encapsulated in liposomes and suspended in a PBS/ISA51 water-in-oil emulsion, followed by dermal application of Aldara™ ointment (5% imiquimod) to the site of administration within 15-20 hours (diamonds). In contrast, 90% of mice had palpable tumors 20 days after treatment with PBS alone (triangles) and 100% of mice had a palpable tumor after treatment with PBS followed by a dermal application of Aldara (squares).

In one embodiment, tumor size, and the percentage of tumor-bearing mice, was reduced in mice treated with a single administration of a composition comprising CpG ODN and a fusion peptide encapsulated in liposomes with suspended in a water-in-oil emulsion, followed by a dermal application of Aldara ointment at the site of treatment administration (FIGS. 18 and 19).

The compositions as described herein may be formulated in a form that is suitable for oral, nasal, rectal or parenteral administration. Parenteral administration includes intravenous, intraperitoneal, intradermal, subcutaneous, intramuscular, transepithelial, intrapulmonary, intrathecal, and topical modes of administration. The preferred routes are intramuscular, subcutaneous and intradermal to achieve a depot effect.

The compositions as described herein may be effective when administered in a single application.

In another embodiment, the compositions as described herein may be used in combination, before or after, other cancer therapies such as radiotherapy and chemotherapy. It has been previously shown that melanoma recurrence was prevented when patients diagnosed with stage II or III melanoma were treated surgically, then given a vaccine composition comprising a composition to induce a CTL response to melanoma-specific antigens. (Antonia, S. J. et al., *Clin. Cancer Res.* 12:878-887, 2006; Allegra, C. J. and R. W. Childs., *J. National Cancer Inst.* 97:1396-1397, 2005; Cassarino, D. S. et al., *J. Cutaneous Path.* 33:335-342, 2006; Correale, P. et al., *J. National Cancer Inst.* 97:1437-1445, 2005; Gulley, J. L. et al., *Clin. Cancer Res.* 11: 3353-3362, 2005; and Chakraborty, M. et al., *Cancer Res.* 64:4328-4337, 2004).

The invention is further illustrated by the following non-limiting examples.

EXAMPLES

Example 1

Cellular Response
(a) Activation

To examine the specificity and rapidity of the CTL response, mice were treated once with a composition comprising CpG ODN adjuvant, a CTL epitope of human papilloma virus (HPV) 16, namely R9F (E7 (H2-Db) peptide RAHYNIVTF, amino acids 49-57; SEQ ID NO: 1) fused to PADRE (AKXVAAWTLKAAA-OH (SEQ ID NO: 10); 50 µg/dose), which is a universal T helper epitope, and encapsulated in liposomes (0.2 g lecithin and 0.02 g cholesterol/dose) suspended in a PBS/FIA (phosphate buffered saline/Freund's incomplete adjuvant) emulsion (100 µl/dose). Fourteen days post-treatment, splenocytes (effector cells) were co-cultured for 6 hours with R9F or an irrelevant peptide (KIMCNSSCM; SEQ ID NO: 13). An ex vivo intracellular IFN-γ staining of splenocytes demonstrated that the proportion of IFN-γ positive CD8+ T cells (CTLs) was 13 fold higher (1.6% of splenocytes) when splenocytes were exposed to R9F peptide than when splenocytes were exposed to the irrelevant peptide (0.12% of splenocytes or no peptide; FIG. 1). As demonstrated in FIG. 1, treatment of mice with the above-described composition comprising R9F peptide caused a significant expansion of CTLs that exhibit a specific response to stimulation by HPV epitope, as compared to mice treated with a composition comprising irrelevant peptide.

Figure 2:
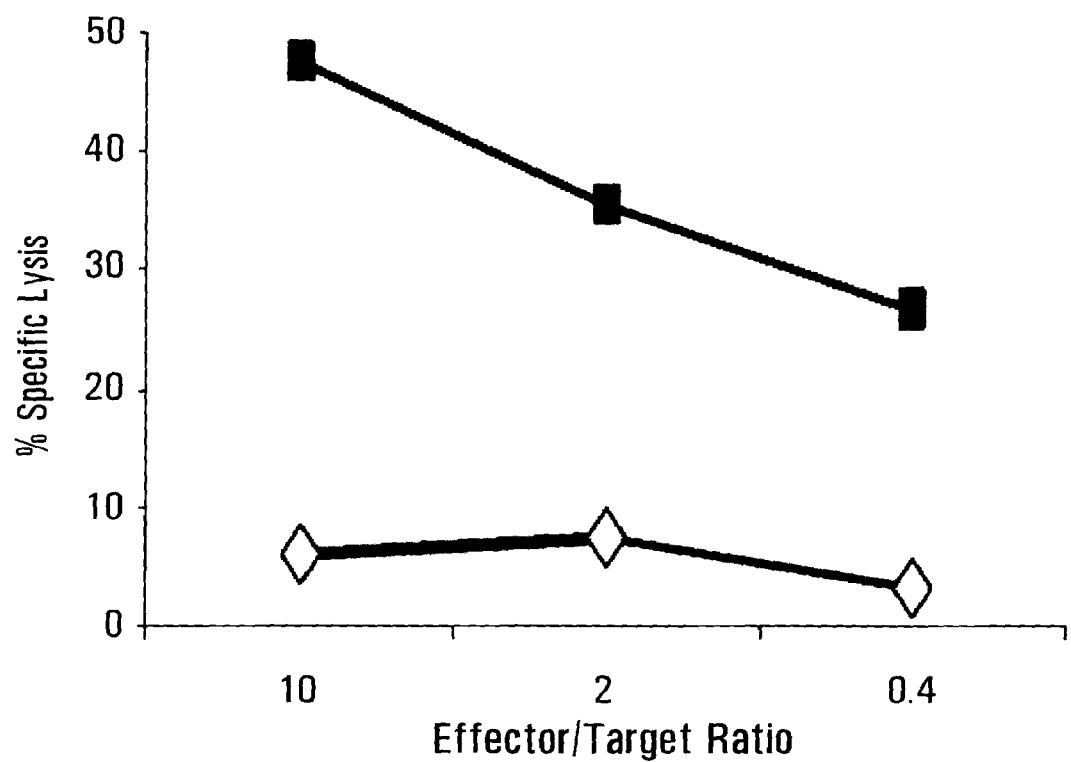
FIG. 2 illustrates lysis of R9F peptide (SEQ ID NO: 1) loaded (squares) and irrelevant peptide loaded (diamonds) EL-4 cells by splenocytes from mice treated 30 days prior with a composition comprising R9F peptide fused with PADRE (SEQ ID NO: 10), and encapsulated with CpG ODN (SEQ ID NO: 12) in liposomes suspended in a PBS/FIA water-in-oil emulsion.

Intracellular lymphokine staining demonstrated the presence of IFN-γ positive CTLs. To demonstrate the protective function of IFN-γ producing CTLs, mice were treated with a composition comprising CpG ODN and R9F peptide fused with PADRE and encapsulated in liposomes suspended in a water-in-oil emulsion. Thirty days post-treatment, R9F peptide (RAHYNIVTF; SEQ ID NO: 1) loaded E4 cells (target cells; mouse lymphoma cell line) and an irrelevant peptide (KIMCNSSCM; SEQ ID NO: 13) loaded E4 cells were stimulated in vitro for 6 days with splenocytes from treated mice. Cytotoxicity was measured by JAM assay (FIG. 2). After the 6-day in vitro stimulation, approximately 50% of R9F peptide loaded EL-4 cells (Effector to Target ratio 10) were lysed by splenocytes from mice treated with the composition comprising R9F peptide (squares). In contrast only approximately 5% of irrelevant peptide loaded EL-4 cells were lysed by the same splenocytes (diamonds; p<0.009).

(b) Duration

The duration of the memory response induced by a single treatment with a particular embodiment of the invention was demonstrated (FIG. 3) by the lysis of EL-4 cells by splenocytes obtained from mice 130 days post-treatment with the following compositions: (i) fused peptide (R9F peptide fused with PADRE) and CpG ODN encapsulated in liposomes contained in a PBS/FIA water-in-oil emulsion (diamonds); (ii) unencapsulated fused peptide and CpG ODN in a PBS/FIA water-in-oil emulsion (triangles and crosses); or (iii) liposome encapsulated fused peptide in a PBS/FIA water-in-oil emulsion without a CpG ODN adjuvant (closed circles). Splenocytes treated with liposome-encapsulated fused peptide, liposome-encapsulated CpG ODN, unencapsulated-fused peptide and CpG ODN, and unencapsulated-fused peptide alone served as control splenocytes.

The JAM assay used a six-day in vitro stimulation followed by co-culturing splenocytes (effector cells) with R9F or irrelevant peptide-loaded EL-4 cells (target cells) that had been preloaded with $^3$H-labelled thymidine. Splenocytes from mice immunized with fused peptide and CpG ODN encapsulated in lipsomes suspended in a water-in-oil emulsion lysed 30% of the R9F peptide loaded target cells when the effector to target ratio was 25:1 and 5:1 and 15% of the target cells when the ratio was 1:1 (FIG. 3). Splenocytes from mice given the control treatment demonstrated cytotoxicity at background levels. Duration of a CTL response for >130 days following a single treatment is remarkable in relation to the duration of CTL responses reported in the literature.

Example 2

Eradication of Cervical Cancer

Figure 4:
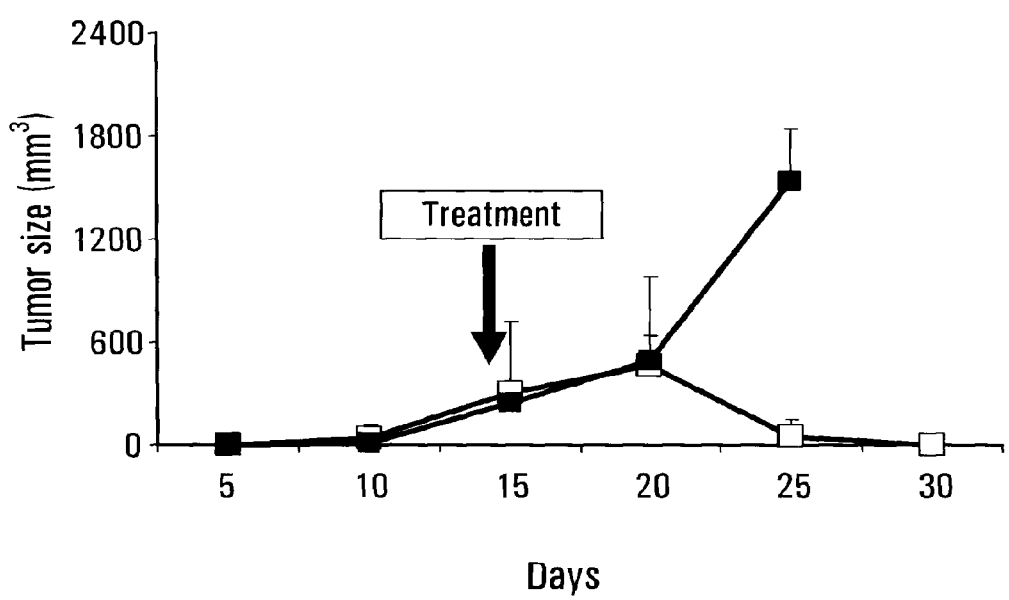
FIG. 4 illustrates the effect of a single administration of a composition comprising CpG ODN, a fusion peptide (R9F peptide (SEQ ID NO: 1) fused with PADRE (SEQ ID NO: 10)) encapsulated in liposomes suspended in a PBS/FIA water-in-oil emulsion (open squares) on the size of 14-day C3 tumors in mice. Tumors were undetectable by palpation by day 30 (16 days post-treatment). In contrast, C3 tumors in mice given a control treatment comprising the composition as described above in the absence of a fusion peptide (closed squares) continued to increase in size. All mice (n=10) were challenged with 0.5×10$^6$ C3 tumour cells 14 days prior to treatment. The difference in size of tumors in the two treatment groups was statistically significant (p=0.002 at day 25).

Despite the development of preventative vaccines for human papillomavirus (HPV) induced cervical and vulvar cancer, for example, Gardasil™ and Cervarix™, a therapeutic treatment for cervical and vulvar cancer remains a high priority. In this example, a treatment composition comprising a CTL epitope of human papilloma virus (HPV) 16, namely R9F (E7 (H2-Db) peptide RAHYNIVTF, amino acids 49-57; SEQ ID NO: 1) was used to induce CTLs. These CTLs need CD4+ T cell help for their differentiation and expansion, as well as their maturation into functional memory CTLs. To achieve a potent CTL response through CD4+ T cell help, R9F peptide was fused to the universal T helper epitope, PADRE (SEQ ID NO: 10), yielding a fusion peptide. The fused peptide was encapsulated in liposomes together with synthetic oligdeoxynucleotides containing CpG ODN motifs or lipopeptide (Pam3Cys-SKKKK). The therapeutic composition used a PBS/FIA water-in-oil emulsion to deliver the therapeutic formulation in a single treatment. Efficacy of the therapeutic treatment was demonstrated using HPV 16-expressing C3 tumor cells to challenge C57BL/6 mice (10 mice/group), then treating the mice on day 14 post-challenge with the treatment composition described above or a control composition. By day thirty (i.e., 16 days post-treatment), complete eradication of palpable tumors was demonstrated in all 10 mice in the group challenged with the C3 tumor then given treatment (FIG. 4; open squares). In contrast, tumors in all 10 control mice treated with a composition comprising all the components of the therapeutic treatment described above except fused peptide, continued to increase in size (closed squares).

Example 3

Prophylaxis

To further demonstrate the ability of a composition of the invention to protect against an in vivo challenge with C3 tumor cells, female C57BL/6 mice were injected subcutaneously at the base of the tail with a composition comprising R9F peptide (RAHYNIVTF; SEQ ID NO: 1) fused with PADRE (SEQ ID NO: 10) (referred to as fused peptide) and encapsulated with CpG ODN in liposomes suspended in a water-in-oil emulsion. To determine if the composition would be as protective as a composition comprising a replacement adjuvant to CpG ODN, mice were administered a composition as described above wherein CpG ODN was replaced by an alternative CpG adjuvant, namely, Pam3c (Pam3Cys-sKKKK). Control groups were injected with PBS, CpG ODN in PBS, fused peptide in PBS, fused peptide suspended in PBS with CpG ODN, or fused peptide encapsulated in liposomes with no adjuvant.

Figure 5:
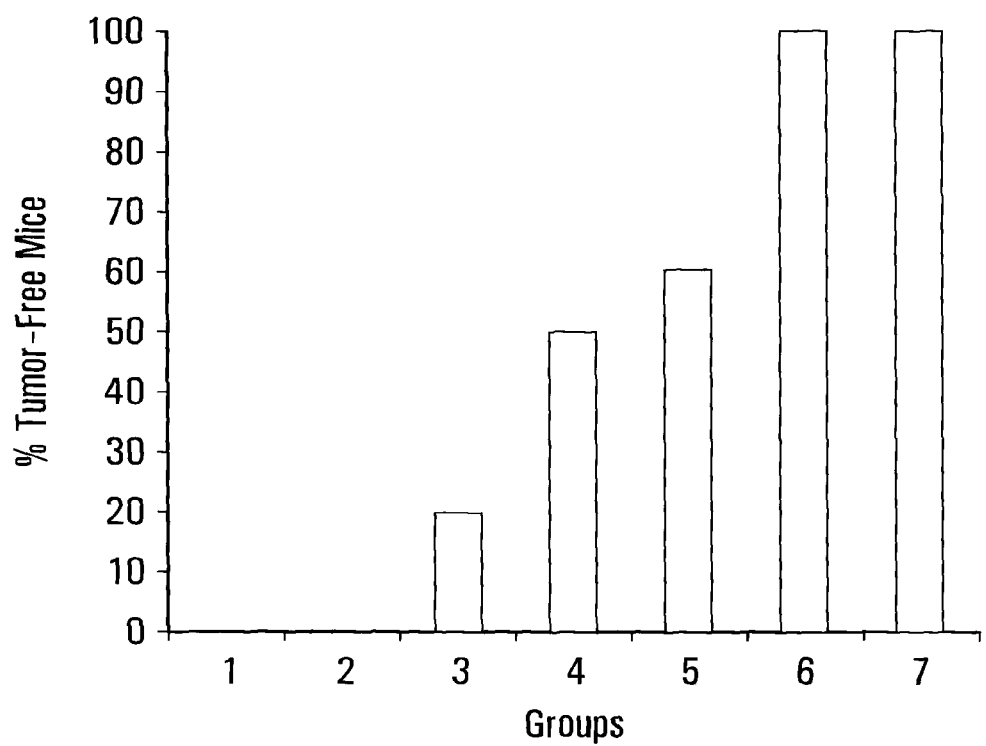
FIG. 5 illustrates the effect of prophylactic treatment on the percentage of mice that are tumor-free 61 days post-challenge with 0.5×10$^6$ C3 cells. Treatment groups consisted of mice treated with one of the following compositions comprising: (1) PBS; (2) CpG in PBS; (3) fusion peptide (R9F peptide (SEQ ID NO: 1) fused with PADRE (SEQ ID NO: 10)) in PBS; (4) fusion peptide encapsulated in liposomes suspended in a PBS/FIA water-in-oil emulsion; (5) fusion peptide and CpG ODN in a water-in-oil emulsion; (6) fusion peptide and CpG ODN encapsulated in liposomes; (7) fusion peptide and the lipopeptide, Pam3Cys-SKKKK (Pam3c) encapsulated in liposomes suspended in a water-in-oil emulsion.

Fifteen days after a single treatment, $0.5 \times 10^6$ C3 cells were implanted subcutaneously in the left flank of treated mice as a primary challenge (FIG. 5). All mice injected with PBS or CpG ODN in PBS developed tumors within 2 weeks and had to be removed from the study by day 30 based on tumor size as required by animal care protocols. Treatment with fused peptide in PBS protected only 20% of mice (treatment group 3). Fused peptide encapsulated in liposomes in a PBS emulsion prevented 50% of the mice from developing tumors (treatment group 4), suggesting that liposome encapsulated fused peptide offers some protection from the C3 challenge. Treatment with fused peptide and CpG ODN in a PBS emulsion prevented 60% of mice from developing tumors (treatment group 5). In comparison, 100% of mice treated with fused peptide encapsulated in liposomes with CpG ODN remained tumor-free during the 61 day post-challenge monitoring period (treatment group 6). To determine the duration and magnitude of the memory response directed against the tumors, mice in treatment group 6 were given a secondary challenge of $6 \times 10^6$ C3 tumor cells. All mice remained tumor-free for a further 73 days, demonstrating that a single treatment of a composition of the invention provides a robust and long-lasting cellular immune response. Similarly, replacement of CpG with Pam3c resulted in all mice remaining tumor free for 61 days (treatment group 7). These mice were not re-challenged with C3 cells.

Therapy

To evaluate treatment of established palpable C3 tumors, mice were implanted with $0.5 \times 10^6$ C3 cells subcutaneously in the left flank. On either day 4, 5, 6 or 9 post-tumor implantation, mice (n=10) were treated with a composition comprising CpG ODN and R9F peptide (RAHYNIVTF; SEQ ID NO: 1) fused with PADRE (SEQ ID NO: 10) (fused peptide) and encapsulated in liposomes and suspended in a PBS/FIA water-in-oil emulsion a placebo (fused peptide and CpG ODN in a PBS emulsion). A single immunization eradicated tumors by day 40 in all 10 mice in the treatment groups that were immunized 4, 5 or 6 days post-tumor implantation and all 30 mice in the group that was immunized 9 days post-tumor implantation. Only one mouse maintained a tumor until day 40 in the group treated on day 5 post-tumor implantation (Table 1). In contrast, 9/10 mice developed tumors in the groups treated with the placebo composition on day 4 or 6 days post-tumor implantation. In the group of mice administered with the placebo 5 days post-challenge, 10/10 mice developed tumors and 27/30 mice developed tumors in the group treated with the placebo vaccine on day 9 post-tumor implantation.

To evaluate whether replacement of CpG ODN with Pam3c would alter the ability of a composition to eradicate C3 tumors, ten mice were treated with a composition comprising fused peptide encapsulated with Pam3c in liposomes and suspended in a PBS/FIA water-in-oil emulsion or a placebo treatment comprising the same composition, but without liposomes was used to treat a second group of 10 mice. Mice in the two treatment groups were subsequently challenged with $1 \times 10^6$ C3 cells in the left flank. Therapeutic treatment of established C3 tumors using fused peptide encapsulated with an Pam3c in liposomes was repeated twice with similar results as reported in Table 1.

TABLE 2

Eradication of tumors in mice treated with a composition comprising R9F peptide (SEQ ID NO: 1) fused with PADRE (SEQ ID NO: 10) (fused peptide) and in liposomes and suspended in a water-in-oil emulsion containing CpG ODN or Pam3c (*) as adjuvants or a placebo vaccine comprising all of the above components except liposomes.

| Treatment (Number of days post- tumor implantation) | Number of mice with tumors (day 40 post-challenge | |
|---|---|---|
| | Placebo | Treated |
| 4 | 9/10 | 0/10 |
| 5 | 10/10 | 1/10 |
| 6 | 9/10 | 0/10 |
| 9 | 27/30 | 0/30 |
| 9* (with Pam3c) | 9/10 | 0/10 |

Example 4

A Therapeutic Treatment of Melanoma

Tyrosinase is a protein overexpressed in melanoma. Peptides from tyrosinase protein are generally poor antigens for treatment of melanoma. As described herein, V8L, a peptide from tyrosinase-related protein (TRP-2) (amino acids 181-188; VYDFFVWL; SEQ ID NO: 6) that binds to murine MHC, $H2K^2$ and human HLA-A2.1 was used in a therapeutic treatment to stimulate production of IFN-γ producing cells. Stimulation of the number of TRP-2 specific IFN-γ producing cells indicates that a therapeutic effect directed specifically against melanoma can be anticipated.

C57BL mice were treated once with a composition of the invention comprising CpG ODN and TRP-2 peptide fused to PADRE encapsulated in liposomes suspended in a water-in-oil emulsion. Control treatments were carried out with a composition comprising liposome encapsulated TRP-2 peptide with PADRE in the absence of CpG ODN, and a composition comprising CpG ODN and an irrelevant peptide (KIMCNSSCM; SEQ ID NO: 13) with PADRE encapsulated in liposomes. In both control treatments, the liposomes were suspended in a PBS/ISA51 water-in-oil emulsion. Ex vivo detection of IFN-γ producing splenocytes by ELISPOT indicated that the treatment composition produced the greatest number of TRP-2 specific IFN-γ producing cells (FIG. 6, group A). The control treatment (FIG. 6, group B) produced about half as many TRP-2 specific IFN-γ producing cells and replacement of TPR-2 by an irrelevant peptide produced background levels of TRP-2 specific IFN-γ producing cells (FIG. 6; group C), showing that the treatment composition of the invention produces the largest number of TRP-2 specific IFN-γ producing cells that are required to combat melanoma cancer.

Example 5

A Therapeutic Treatment of Breast Cancer

The p53 gene product is an ideal and widely expressed target for therapy of malignancies, in particular, breast cancer. A large portion of human cancers exhibits p53 mutations as an early event in tumorigenesis. Overexpression of p53 is an independent predictor of more aggressive cancer, lymph node metastases, failure of standard therapeutic regimens, and ultimately of cancer-related mortality.

Mice treated with a single treatment with a composition of the invention comprising a modified p53 CTL epitope, mK9M, (KYICNSSCM; SEQ ID NO: 8) with CpG ODN and PADRE (SEQ ID NO: 10) encapsulated in liposomes in a PBS/ISA51 water-in-oil emulsion produced approximately 10 to 40 times more p53 peptide specific IFN-γ producing cells (FIG. 7; group A) than mice treated with a composition comprising the peptide fused to PADRE and CpG ODN in the absence of liposomes (FIG. 7; group B); a composition comprising fused peptide encapsulated in liposomes without CpG ODN; or a composition in which the fused peptide was replaced by an irrelevant peptide (FIG. 7; group D). Increased production of tumor specific IFN-γ producing cells is correlated with a reduction/eradication of cervical cancer tumors (see Examples 2 and 3), therefore, one skilled in the art would predict a similar result for p53 bearing tumors.

Example 6

Therapeutic Cancer Treatment against more than One Target

Some cancers express more than one tumor-associated protein simultaneously. Such cancers offer more than one target for therapeutic treatment. For example, melanoma cells overexpress both p53 and TRP raising the possibility that treatments aimed at both p53 and TRP simultaneously could be more effective and specific since cells expressing both p53 and TRP targets would be more vulnerable to treatment.

Mice treated with a single administration of a composition comprising a mixture of p53 (mK9M; KYICNSSCM; SEQ ID NO: 8) and TRP-2 (V8L; VYDFFVWL; SEQ ID NO: 6) peptides with CpG ODN and PADRE (AKXVAAWTLKAAA, wherein X=cyclohexylalanyl); SEQ ID NO: 10) and encapsulated in liposomes suspended in a water-in-oil emulsion produced approximately equal numbers of both p53 and TRP specific IFN-γ producing cells (FIG. 8; group A). In contrast, control mice treated with a mixture of p53 fused to PADRE and TRP-2 CTL peptides with PADRE together with CpG ODN without liposomes produced more TRP-2- than p53- specific IFN-γ producing cells (FIG. 8; group C), even in the absence of CpG ODN (FIG. 8; group B). Production of p53-specific IFN-γ producing cells was at levels obtained with the control treatments (i.e., treatment composition without CpG ODN (group B) or without CpG ODN and liposomes (group D)). These results indicate that mice administered the treatment composition mount a two-pronged attack against tumors bearing TRP-2 and p53 tumor-associated proteins. Without encapsulation of the fused peptides with CpG ODN in liposomes suspended in a water-in-oil emulsion, treated mice attack only one target, the TRP-2 tumor-associated protein, despite being treated with both TRP-2 and p53 peptides.

Example 7

HLA A2 transgenic mice were used, which have a human HLA A2 major histocompatability complex (MHC) gene, and therefore express human MHC, which better mimics human cervical cancer. To be compatible with HLA A2 MHC, CTL epitopes different than those used in the previous examples were utilized. HLA A2 Mice were treated one of the following compositions:

(1) a mixture of four E6/7 human papilloma virus (HPV) derived peptides (MP), the sequence of each peptide being as follows:

```
Y10T (E7: amino acids 11-20; YMLDLQPETT;
SEQ ID NO: 2);

L9V (E7: amino acids 82-90; LLMGTLGIV;
SEQ ID NO: 3);

T81 (E7: amino acids 86-93; TLGIVCPI;
SEQ ID NO: 4);
and

T10V (E6: amino acids 29-38; TIHDIILECV;
SEQ ID NO: 5);
```

2) The above 4 peptides joined together with "aay" linkers into a long peptide (AB2; SEQ ID NO: 14), the sequence of which is as follows:

```
TIHDIILECVaayYMLDLQPETTaayLLMGTLGIVaayTLGIVCPI;
``` or

3) A single peptide selected from the four peptides listed above, namely L9V (E7: amino acids 82-90; LLMGTLGIV; SEQ ID NO: 3).

All treatment compositions comprised PADRE (25 μg/dose) and CpG ODN (50 μg/dose) as adjuvants, and were delivered in liposomes suspended in a PBS/ISA51 water-in-oil emulsion. The mixture of 4 peptides contained 25 μg of each peptide/treatment. The long peptide (AB2) was administered at 100 μg/treatment. The composition comprising L9V alone contained 25 μg/treatment. Control mice were injected with PBS (100 μL/treatment).

Mice were challenged with TC1/A2 tumor cells (1×10$^5$ cells/mouse) implanted subcutaneously in the left flank and tumor size was measured every 5 days. Nineteen days post-challenge, mice (5 mice/group) were treated with one of the above-described compositions, or injected with PBS (controls).

Figure 9:
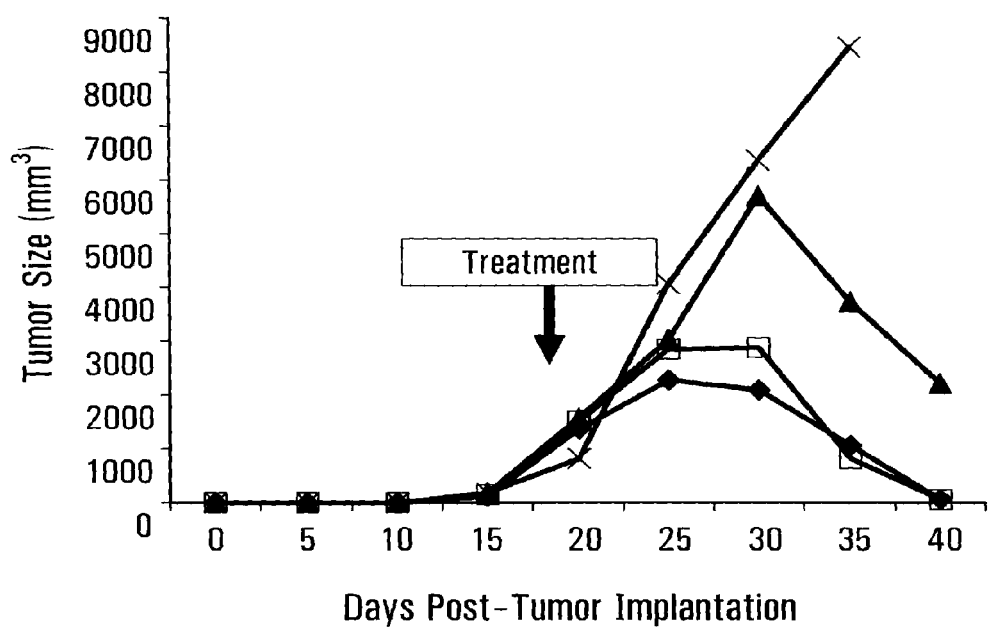
FIG. 9 illustrates the effect of a single treatment with HLA-A2 E6/7 CTL epitope-containing peptides on 19-day-old TC1/A2 established tumors. A single treatment of a composition comprising a mixture of four HPV E6/7 peptides (Y10T (SEQ ID NO: 2), L9V (SEQ ID NO: 3), T81 (SEQ ID NO: 4), and T10V (SEQ ID NO: 5)) encapsulated in liposomes with CpG ODN (SEQ ID NO: 12) and PADRE (SEQ ID NO: 10) then suspended in a PBS/ISA51 water-in-oil emulsion (squares) or a long peptide containing the four HPV E6/7 peptides described above linked together with "aay" (alanine-alanine-tyrosine) linkers (AB2 peptide; SEQ ID NO: 14) encapsulated in liposomes with CpG ODN and PADRE then suspended in a water-in-oil emulsion (diamonds) eradicated TC1/A2 tumors by 21 days post-treatment. Treatment with one E7 peptide of HPV (L9V; SEQ ID NO: 3) encapsulated in liposomes with CpG ODN and PADRE then suspended water-in-oil emulsion significantly reduced tumor size (triangles). Treatment with PBS alone (crosses) did not prevent tumor growth.
Figure 10:
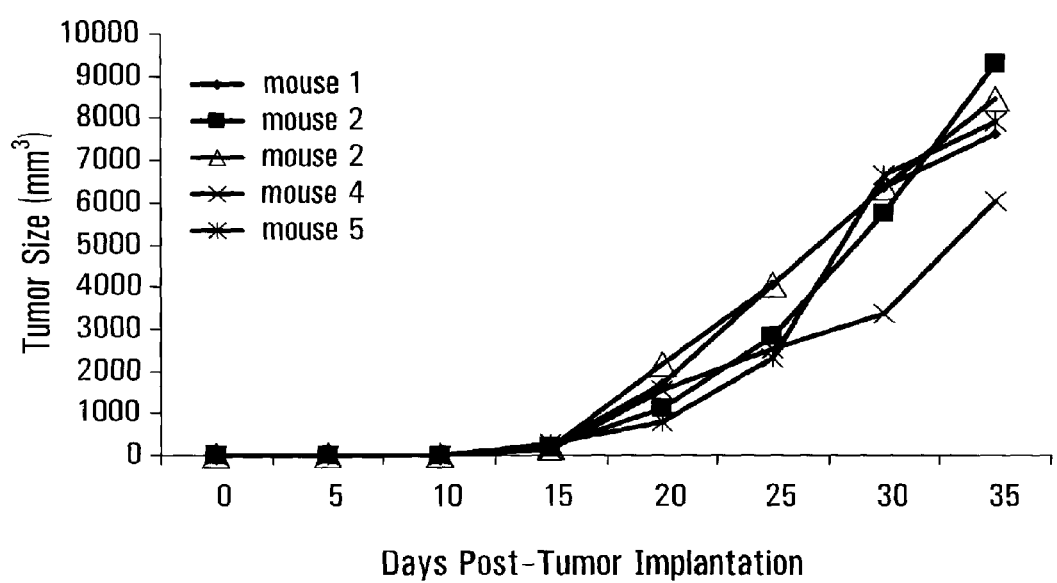
FIG. 10 illustrates tumor growth in five mice injected with PBS alone 19 days post-tumor implantation.

It is shown in FIG. 9 that a single treatment of the composition comprising mixture of the above-described four HPV E6/7 peptides (squares) or the AB2 long peptide (diamonds) eradicated TC1/A2 tumors 21 days post-treatment. Treatment with the composition comprising the E7 peptide L9V significantly reduced tumor size (triangles). Treatment with PBS alone (crosses) did not prevent tumor growth. Tumor growth was similar in all five mice in the control group that received PBS (FIG. 10). All five mice were removed from the study on day 35 as mandated by excessive tumor size. Tumor size is reported as the average tumor size in five mice.

Figure 11:
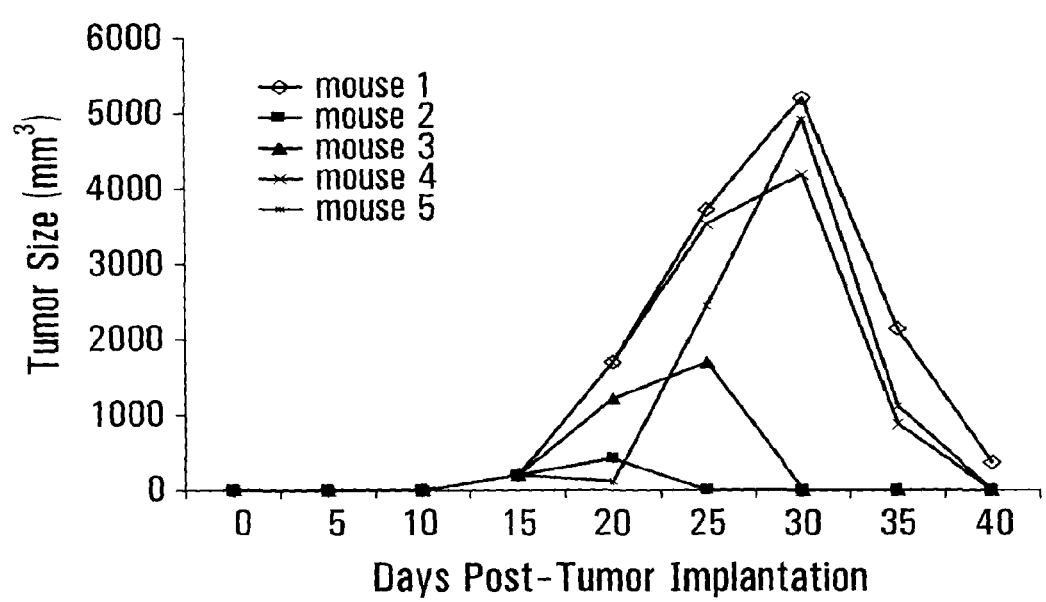
FIG. 11 illustrates the effect of a single treatment with a composition comprising a mixture of four individual HLA-A2 E6/7 CTL epitope-containing peptides (Y10T, L9V, T81, and T10V; SEQ ID NOs: 2, 3, 4 and 5, respectively) encapsulated in liposomes with CpG ODN (SEQ ID NO: 12) and PADRE (SEQ ID NO: 10) then suspended in a PBS/ISA51 water-in-oil emulsion on the growth of 19-day-old TC1/A2 established tumors in five mice.

Reductions in tumor size in mice treated with composition comprising the mixture of peptides was variable (FIG. 11).

Figure 12:
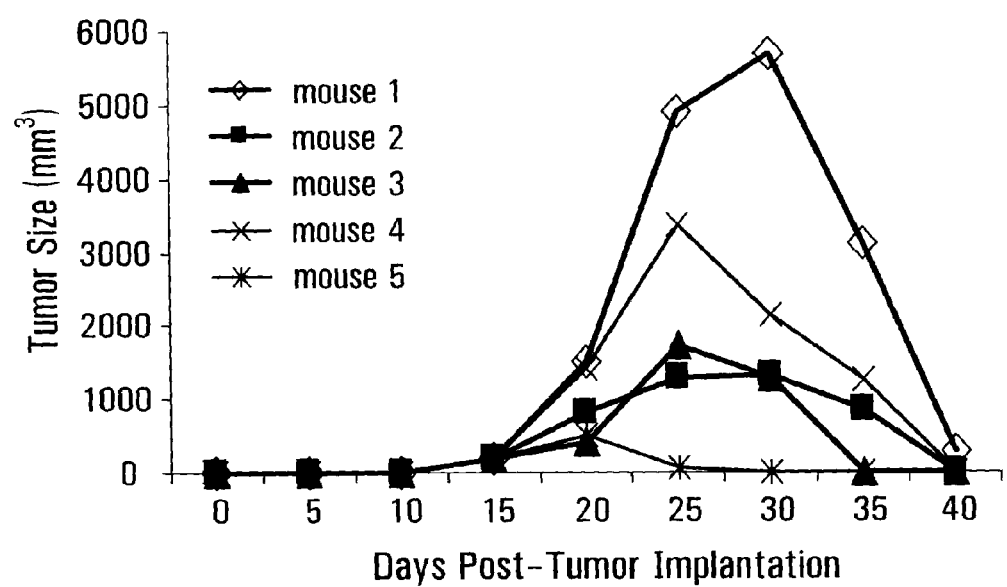
FIG. 12 illustrates the effect of a single treatment with a composition comprising one long peptide (AB2; SEQ ID NO: 14) encapsulated in liposomes with CpG ODN (SEQ ID NO: 12) and PADRE (SEQ ID NO: 10) then suspended in a PBS/ISA51 water-in-oil emulsion on the growth of 19-day-old TC1/A2 established tumors in five mice.

For example, tumor size in mouse 2 was eradicated by day 6 post-treatment. Tumors in the remaining mice were not eradicated until at least day 11 post-treatment. Reductions in tumor size in mice treated with the composition comprising the long peptide (AB2) were also variable (FIG. 12). However, tumors were completely eradicated by day 21 post-treatment in all 5 mice.

Figure 13:
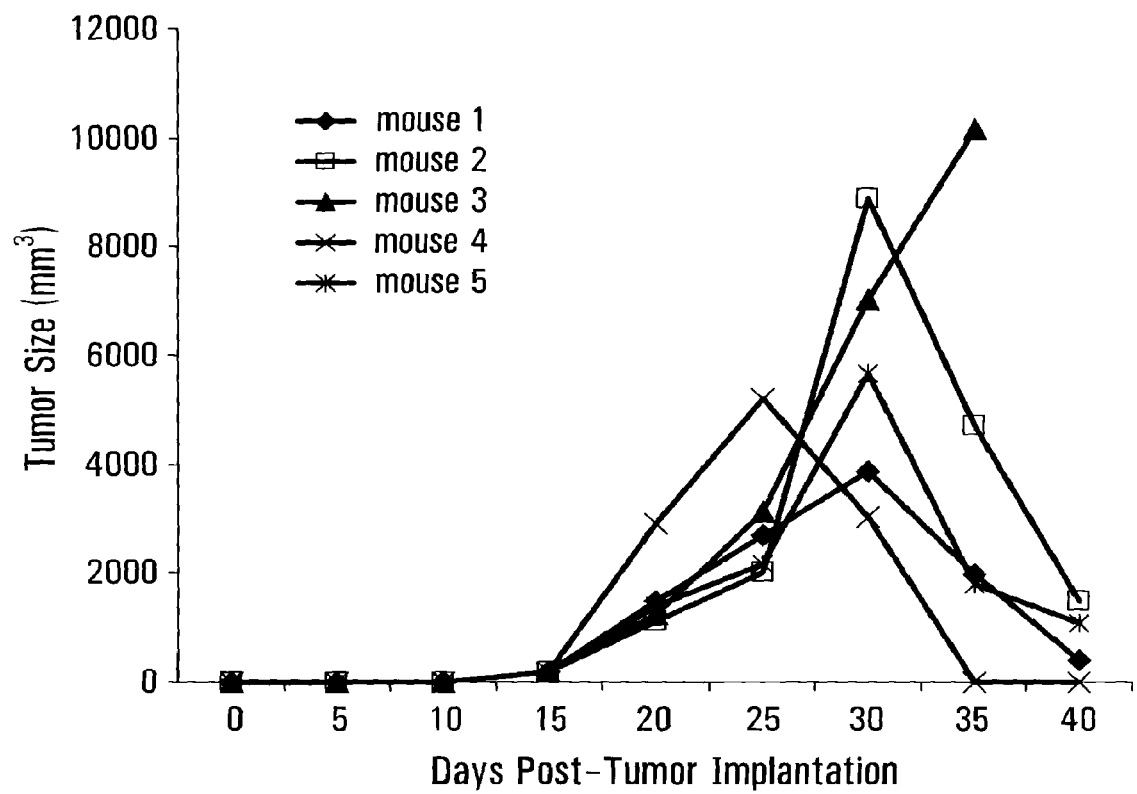
FIG. 13 illustrates the effect of a single treatment with a composition comprising a HLA-A2 E7 CTL epitope (L9V; SEQ ID NO: 3) encapsulated in liposomes with CpG ODN (SEQ ID NO: 12) and PADRE (SEQ ID NO: 10) then suspended PBS/ISA51 water-in-oil emulsion on tumor growth of 19-day-old TC1/A2 established tumors in five mice.

Reductions in tumor size in mice treated with the composition comprising a single HPV E7 peptide (L9V; SEQ ID NO: 3) was similar in 4/5 mice (FIG. 13). Treatment of mouse 3 did not result in tumor size reduction, suggesting that treatment with a composition comprising than one HPV peptide either as a mixture of individual peptides or fused peptides will protect more individuals in a population than immunization against a single peptide.

Example 8

In example 7, four HPV 16 E6/E7 peptides were joined together to form one long peptide using the linker "aay" (-alanine-alanine-tyrosine-). This linker is hydrophobic in nature and adds to the hydrophobicity of the fused long peptide making peptide manufacture difficult and requiring use of dimethyl sulphoxide to solubilize the long peptide.

Figure 14:
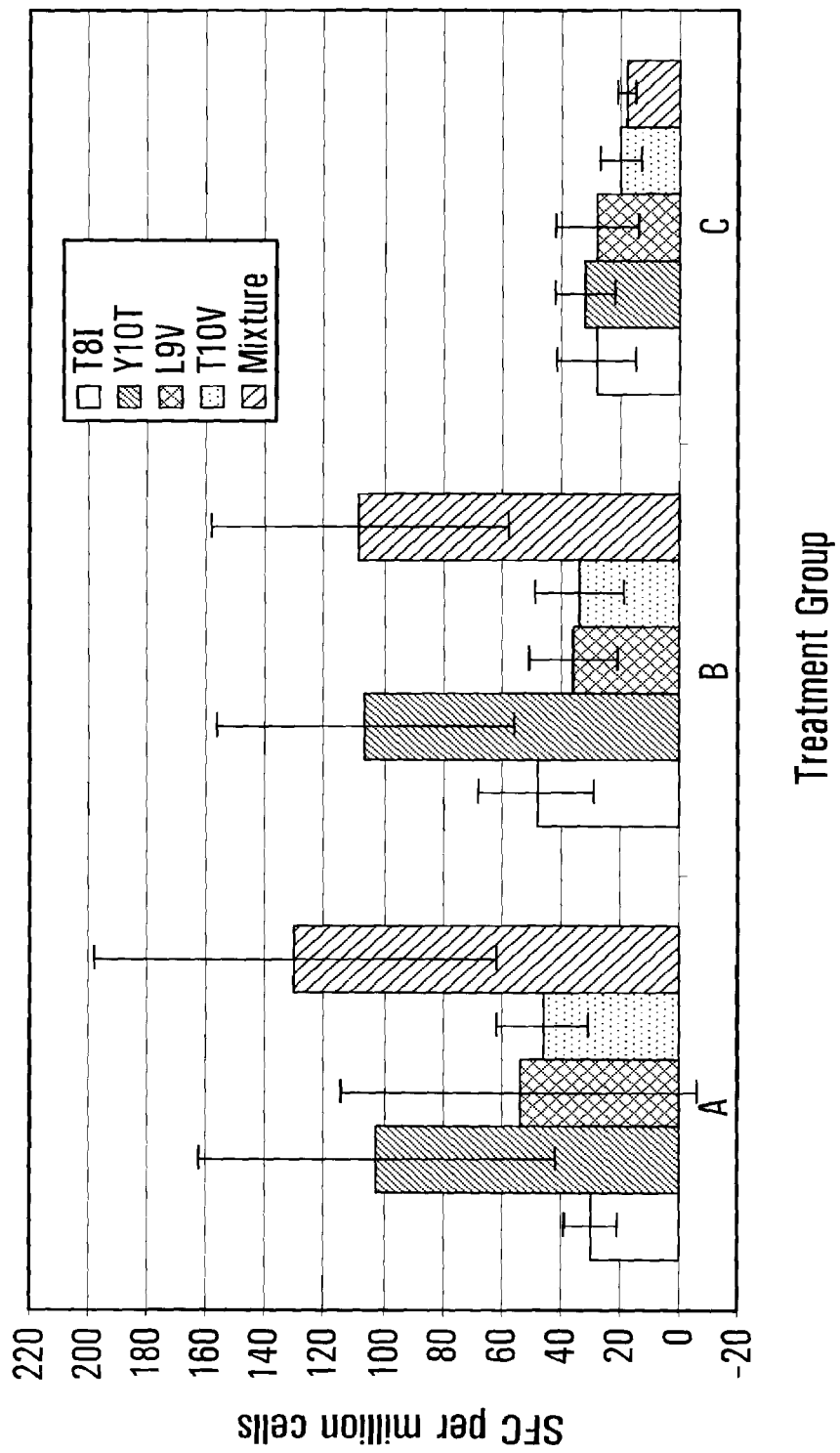
FIG. 14 illustrates ex vivo detection of IFN-γ producing splenocytes in mice 9 days post-immunization by a single administration of a composition comprising (A) four short unlinked HPV-A2 HPV E6/E7 CTL epitope-containing peptides (T81, Y10T, L9V or T10V; SEQ ID Nos: 2, 3, 4 and 5, respectively) or (B) two medium length dipeptides linked together with a "kkp" linker (Y10T-kkp-L9V (SEQ ID NO: 15) and T81-kkp-T10V (SEQ ID NO: 16)). Both compositions were encapsulated in liposomes with CpG ODN (SEQ ID NO: 12) and PADRE (SEQ ID NO: 10) then suspended in a PBS/ISA51 water-in-oil emulsion. Spleens from control mice (C) contained background numbers of splenocytes that could be stimulated with each individual short peptide or a mixture of the four short peptides to produce IFN-γ. In contrast, spleens from mice in the group immunized with either the four short unlinked peptides or two medium dipeptides contained larger numbers of splenocytes that were stimulated with these peptides to produce IFN-γ. Stimulation of splenocytes from mice immunized with either formulation of the invention and stimulated with the mixture of the four short peptides produced approximately five times as many IFNγ-producing splenocytes compared to control splenocytes indicting the linking peptides with "kkp" had no effect on the immune response.

In this example, a "kkp" linker (-lysine-lysine-proline-) was used in place of the "aay" linker to form 2 dipeptides. One dipeptide was Y10T-kkp-L9V (TIHDIILECVk-kpLLMGTLGIV; SEQ ID NO: 15) and the other dipeptide was T81-kkp-T10V (TLGIVCPIkkpYMLDLQPETT; SEQ ID NO: 16). Use of the "kkp" linker resulted in hydrophilic fused peptides that facilitate vaccine manufacture. Using "kkp" to link peptides produced approximately the same number of IFNγ-producing splenocytes as obtained when the same four peptides were used individually (i.e., unlinked (FIG. 14). These results demonstrate that use of kkp linker facilitates manufacture of the vaccine antigen without altering antigen processing and induction of peptide-specific IFNγ-producing splenocytes. Production of these cells is a good indicator of effective eradication of cancer cells.

Example 9

A Therapeutic Treatment against Melanoma

Examples 4, 5 and 6 demonstrate the ability of composition of the invention to increase production of TRP-2 and p53 specific IFN-γ producing splenocytes, thereby, establishing stimulation of a cellular immune responses against melanoma-associated proteins. B16-F10 cells ($10 \times 10^3$ cells/mouse) were implanted subcutaneously in the left flank of pathogen-free C57BL/6 mice. Mice were 6-8 weeks of age at the time of implantation and were housed under filter top conditions with water and food ad libitum. Five days after implantation of melanoma cells, mice received a single treatment by subcutaneous injection of a composition comprising one of two peptides (V8L or S9L (SEQ ID NO: 6 or 7); 25 μg/mouse) derived from TRP-2, one modified peptide (mK9M (SEQ ID NO: 8); 25 μg/mouse) derived from p53 or mixtures of these peptides (25 μg of each peptide/mouse). All compositions also comprised both PADRE (25 μg/mouse) and CpG ODN (50 μg/mouse), and delivered in liposomes suspended in a PBS/ISA51 water-in-oil emulsion Control mice received a single administration of PBS alone. All injections were administered at the base of the tail. Tumor size was determined every 4-5 days using the following formula: longest measurement×(shortest measurement) (Pilon-Thomas et al., J. of Immunother., 29(4), 2006).

Figure 15:
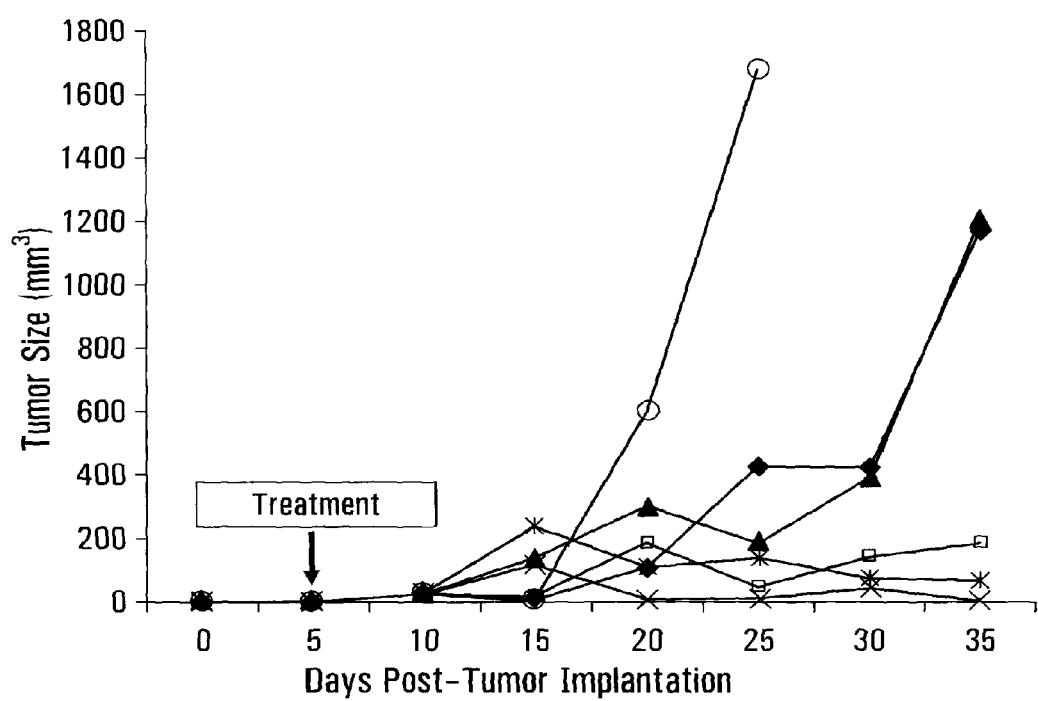
FIG. 15 shows the growth of melanoma tumors in mice treated with one of the following compositions comprising at least one peptide derived from a melanoma-associated protein (TRP-2 or p53) and encapsulated with CpG ODN and PADRE in liposomes suspended in a water-in-oil emulsion: (i) V8L peptide (SEQ ID NO: 6) (diamonds); (ii) S9L peptide (SEQ ID NO: 7) (squares); (iii) mK9M peptide (SEQ ID NO: 8) (triangles); (iv) V8L and mK9M peptides (crosses); and (v) S9L and mK9M peptides (stars). Control mice were treated with PBS alone (circle). Mice were administered the treatment 5 days post-tumor implantation. Each data point is the average size of tumors in five mice.

FIG. 15 demonstrates that mice treated with a composition containing either the V8L (SEQ ID NO: 6)(diamonds) or mK9M peptide (SEQ ID NO: 8) (triangles) inhibited growth of melanoma cells initially, but the melanoma cells overcame the initial inhibition of growth to produce tumors that increased in size to 1200 mm³. Treatment with compositions comprising S9L peptide (SEQ ID NO: 7) (squares) or mixtures of peptides V8L, and mK9M (KYICNSSCM) (crosses), or S9L and mK9M stars) inhibited growth of melanoma for the entire monitoring period. PBS alone (circles) did not have an effect on tumor growth.

Figure 16:
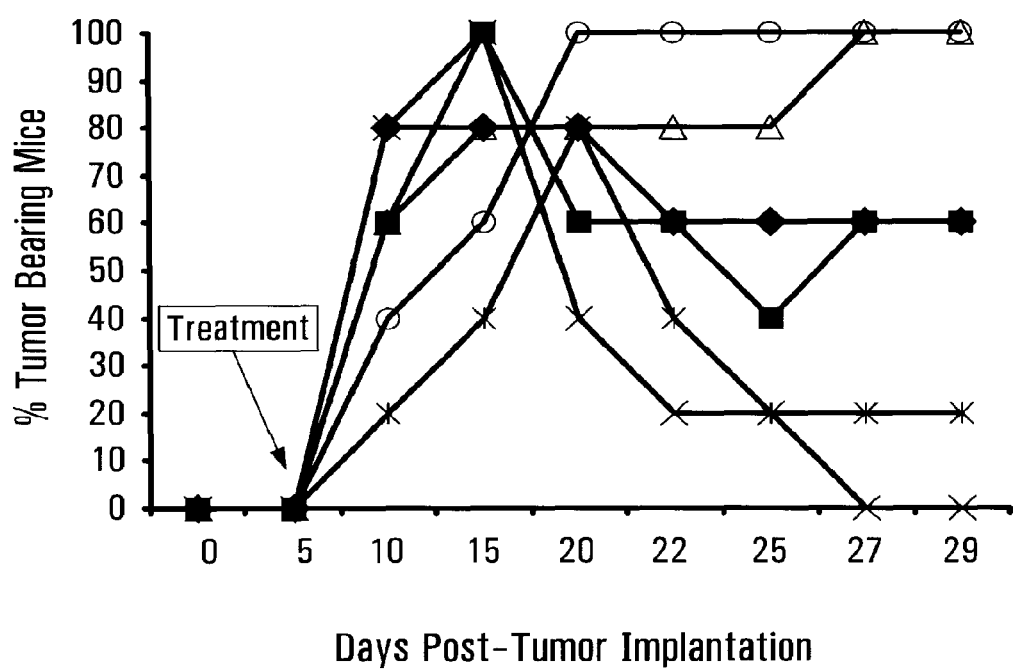
FIG. 16 illustrates the percentage of mice with melanoma tumors after treatment with one of the following compositions comprising at least one peptides derived from a melanoma-associated protein (TRP-2 or p53) and encapsulated with CpG ODN (SEQ ID NO: 12) and PADRE (SEQ ID NO: 10) in liposomes suspended in a PBS/ISA51 water-in-oil emulsion: (i) V8L peptide (SEQ ID NO: 6) (diamonds); (ii) S9L peptide (SEQ ID NO: 7) (squares); (iii) mK9M peptide (SEQ ID NO: 8) (triangles); (iv) V8L and mK9M peptides (crosses); and (v) S9L and mK9M peptides (stars). Control mice were treated with PBS alone (circles). Mice were administered the treatment 5 days post-tumor implantation. Each data point is the average size of tumors in five mice.

Consideration of the percentage of mice that have tumors at the end of the study indicated that vaccine of the invention that contained either the peptide mK9M (SEQ ID NO: 8) (triangles), V8L (SEQ ID NO: 6) (diamonds) or S9L (SEQ ID NO: 7) (squares) cured only 0, 40, and 40%, respectively, of the mice of their tumors (FIG. 16). In contrast, treatment with a composition comprising a mixture S9L and mK9M (stars) cured 80% of the mice of their tumors and or a mixture of V8L and mK9M (crosses) cured 100% of the mice of their tumors.

Example 10

B16 Melanoma Tumor Model

In previous examples, the efficacy of compositions of the invention was demonstrated in established tumors in two independent HPV-cervical cancer models (C3 and TC1/A2). HPV-bearing tumors were eradicated by targeting CTL epitopes of HPV presented on the surface of tumor cells. This strategy is particularly effective when treating virally induced cancers. Tumors presenting over-expressed "self" antigens, however, are more difficult to treat as they are invisible to the immune system. Self antigens are tightly guarded by the tolerance mechanism. An effective therapeutic cancer treatment must have the ability to induce immune responses against over-expressed tumor-associated self antigens. Melanoma (including the B16 tumor model) is believed to down-regulate MHC class I expression and presentation of self antigens. A therapeutic composition for treatment of melanoma must activate low-affinity T cell clonotypes that are capable of targeting self epitopes on the surface of the tumor.

A robust and specific CTL response is required for successful treatment of melanoma by vaccination. In preclinical studies, it has been shown that a B16-specific CTL activity was not sufficient to protect against B16 tumor growth in vivo (Bellone et al., J. of Immunol., 165(5):2651-2656, 2000). Immunotherapy with CpG-matured dendritic cells pulsed with the melanoma-associated self epitope from TRP-2 failed to achieve tumor regression (Pilon-Thomas et al., J. of Immunother., 29(4), 2006). In two other studies, treatment of 5-day old established B16 tumors resulted in tumor eradication in less than 50% of treated mice and tumors reappeared in all treated animals (Pilon-Thomas et al., J. of Immunother., 29(4), 2006; and Bronte et al., Cancer Res., 60:253-258, 2000).

The ability of compositions of the invention to raise effective CTL responses against multiple peptide antigens simultaneously was tested. Mice (5 mice/group) were implanted with $10^4$ B16 cells and treated once 6 days post-implantation with a composition comprising (0.1 ml/dose) 25 μg of a TRP-2 CTL epitope (S9L; SVYD-FFVWL SEQ ID NO: 7), 25 μg of a p53 CTL epitope (mK9M; KYICNSSCM SEQ ID NO: 8), 25 μg of PADRE and 50 μg of CpG ODN per treatment. For comparison, a second group of mice (5 mice/group) were treated a composition comprising either 25 µg of the same TRP-2 CTL epitope or 25 µg of the p53 CTL epitope (K9M; KYMCNS-SCM SEQ ID NO: 9), 25 µg of a modified p53 CTL epitope, mK9M (SEQ ID NO: 8), 25 µg of PADRE (AKXVAAW-TLKAAA, wherein X=cyclohexylalanyl; SEQ ID NO: 10) and 50 µg of CpG ODN per treatment. All components of the composition were incorporated in the liposomes before emulsification in the hydrophobic carrier, ISA51. Control mice were treated with PBS alone.

Figure 17:
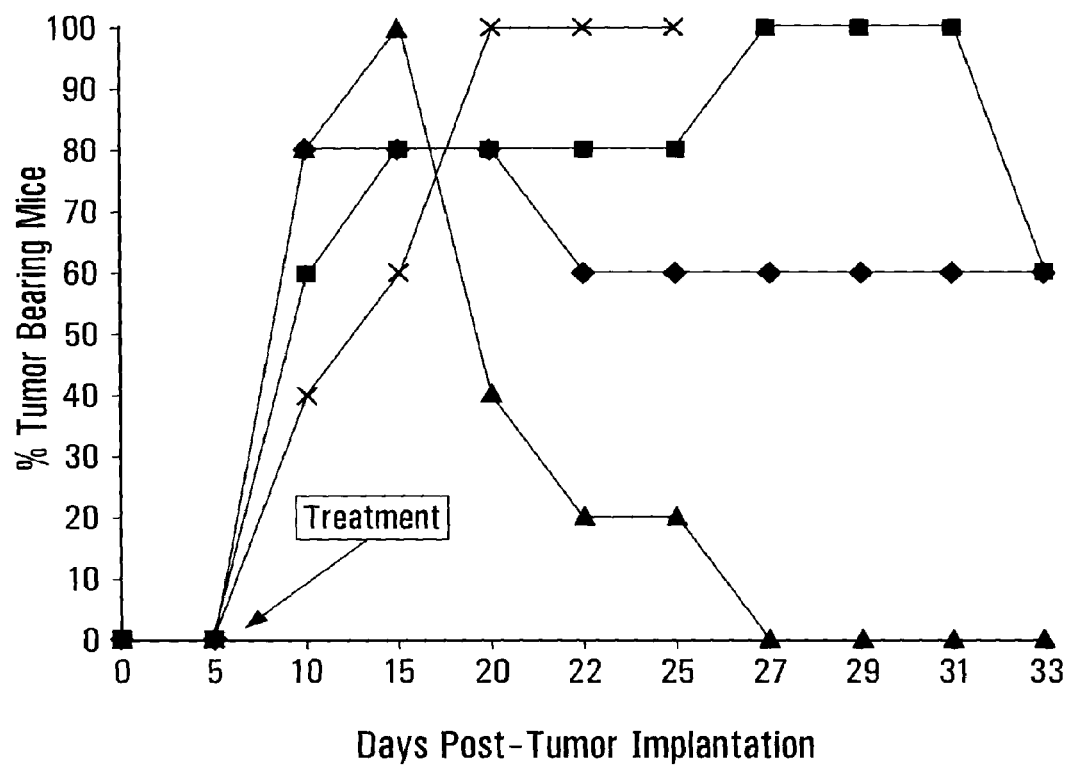
FIG. 17 illustrates the eradication or reduction of 6-day-old established B16 tumors in mice upon a single treatment with a composition comprising CpG ODN (SEQ ID NO: 12), PADRE and a TRP-2 and/or a p53 CTL epitope, encapsulated in liposomes which were suspended in PBS then emulsified in ISA51. A single treatment with a mixture of TRP-2 and p53 CTL epitopes rendered all mice tumor-free by 21 days post-administration (triangles). A single treatment with TRP-2 (diamonds) or p53 (squares) alone rendered 40% of the mice tumor-free 33 days post treatment. Treatment with PBS in controls mice had no effect on the progression of tumors (crosses).

A single treatment with the composition containing a mixture of the TRP-2 and p53 epitope eradicated tumors in all mice 21 days post-treatment (FIG. 17; triangles), whereas treatment with a composition containing TRP-2 (diamonds) or p53 alone (squares) cleared tumors in only 40% of mice. All control mice injected with PBS developed tumors (crosses).

Example 11

Mice (C57BL/6) were challenged with C3 tumors that developed into palpable size by 8 days post-challenge. On day 8 post-challenge, mice were divided into two control groups (10 mice/group), and a treatment group that was treated with a single administration of a composition comprising CpG ODN and a fusion peptide (R9F peptide (SEQ ID NO: 1) fused to PADRE (SEQ ID NO: 10) encapsulated in liposomes with suspended in a water-in-oil emulsion.

Within 15-20 hours following treatment, mice received a dermal application of Aldara™ ointment (25 mg (equivalent to 10-12 µl Aldara)) at the site of treatment administration. The active ingredient in Aldara is imiquimod at a concentration of 5%. Imiquimod (1-(2-methylpropyl)-1H-imidazo [4,5-c]quinolin-4-amine) is a novel synthetic compound that is a member of the imidazoquinolone family of drugs known to have the properties of topical immune response modifiers and stimulators. Imiquimod is a ligand for TLR7 and activates a Th1-like cytokine milieu that includes IFN-α, TNF-α, IL-1α, IL-6, and IL-8. In contrast, the two control groups received either PBS alone (100 µL/mouse) or PBS followed by a dermal application of Aldara ointment (25 mg). Tumour size was reduced in mice given the treatment composition followed by dermal application of Aldara (FIG. 18; crosses), but not reduced in controls given PBS alone (crosses) or PBS followed by application of Aldara (triangles). FIG. 19 shows that the percentage of tumor-bearing mice was reduced in mice given the treatment composition followed by dermal application of Aldara (diamonds), but not reduced in controls given PBS alone (triangles) or PBS followed by application of Aldara (squares).

Example 12

Treatment of Melanoma Using Tetanus a Toxoid Peptide F21E as a T-helper Epitope

A melanoma-related antigen, TRP-2, in combination with a T-helper epitope derived from tetanus toxoid, were encapsulated together in a composition comprising CpG ODN in a PBS/ISA51 water-in-oil emulsion. Tetanus toxoid peptide replaced PADRE, the T-helper epitope used in previous examples, to demonstrate that a variety of T-helper epitopes can be used. Stimulation of the number of TRP-2 peptide-specific IFN-γ producing cells indicates that a therapeutic effect directed specifically against melanoma can be anticipated.

Figure 20:
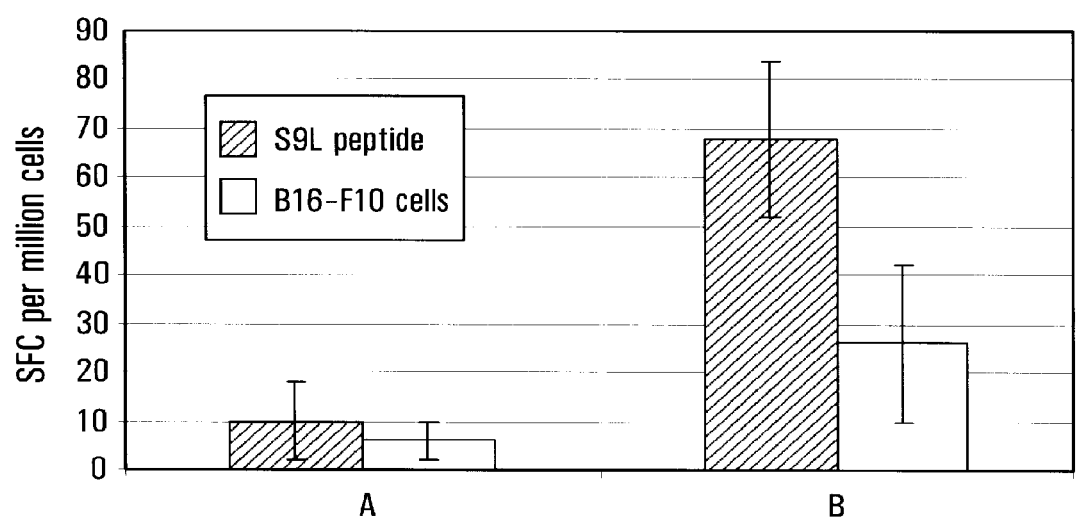
FIG. 20 illustrates ex vivo detection of IFN-γ producing splenocytes exposed to the melanoma-related antigen, TRP-2 (S9L peptide; SEQ ID NO: 7), or B16F10 cells, 8 days post-immunization with a single administration of a treatment composition comprising S9L peptide and a tetanus toxoid epitope (F21E; SEQ ID NO: 11) encapsulated together in liposomes with CpG ODN (SEQ ID NO: 12) in a PBS/ISA51 water-in-oil emulsion (B). Control mice were immunized with the above-described composition formulated without the tetanus toxoid T helper epitope (A). Five times as many splenocytes that were stimulated with B16-F10 cells to produce IFN-γ were present in spleens from the group immunized with the treatment composition of the invention compared to the control group.

C57BL mice were immunized with a composition comprising a TRP-2 peptide (S9L; SEQ ID NO: 7) and the tetanus toxoid epitope F21E (amino acids 947-967, FNN-FTVSFWLRVPKVSASHLE; SEQ ID NO: 11) encapsulated together in liposomes with CpG ODN. Control mice were immunized with the above-described composition formulated without the tetanus toxoid T helper epitope. Ex-vivo detection of IFN-γ was performed by ELISPOT on splenocytes isolated from spleens collected 8 days post-immunization. Splenocytes of control and treated mice were plated at $5 \times 10^5$ cells per well and were stimulated in vitro with the TRP-2 peptide (S9L), or with the melanoma cancer cell line B16-F10 ($5 \times 10^4$ cells per well, 1:10 effector to target ratio). Splenocytes of mice immunized with the treatment composition contained the largest number of TRP-2 specific IFN-γ producing cells. The immune response was observed when splenocytes were stimulated with the TRP-2 peptide or with the B16-F10 cells (FIG. 20). Spleens from control mice demonstrated background levels of TRP-2 specific IFN-γ producing cells. Thus, a strong anti-melanoma CTL immune response can be detected when the splenocytes are stimulated using the TRP-2 peptide in the presence of a tetanus toxoid epitope, but also using the melanoma antigens present on the surface of B16-F10 cells.

Methods

Cell Lines

The C3 cell line was maintained in Iscove Modified Dulbecco's Medium (IMDM; Sigma, St Louis, Mo.) supplemented with 10% heat-inactivated fetal calf serum (Sigma, St Louis, Mo.), 2 mM L-glutamine (Gibco, Burlington, ON), 50 mM 2-mercaptoethanol (Gibco, Burlington, ON), 100 U/ml penicillin and 100 µg/ml streptomycin (Gibco, Burlington, ON). Cells were incubated at 37° C./5% $CO_2$.

The EL-4 cell line is a lymphoma cell line that originated in mice. The EL-4 cell line was maintained in Dulbecco's Modified Eagle Medium (DMEM; Sigma, St Louis, Mo.) with high glucose content containing 2 mM L-glutamine, and supplemented with 10% heat-inactivated fetal calf serum (Sigma, St Louis, Mo.), 50 mM 2-mercaptoethanol (Gibco, Burlington, ON), 100 U/ml penicillin and 100 µg/ml streptomycin (Gibco, Burlington, ON). Cells were incubated at 37° C./5% $CO_2$.

The B16F1 (B16) melanoma cell line was obtained from American Type Culture Collection (ATCC), Manassas, Va.

Peptides

The HPV 16 E7 (H-2D$^b$) peptide RAHYNIVTF$^{49-57}$ (R9F) containing a CTL epitope was fused to PADRE containing a CD4$^+$helper epitope by Dalton Chemical Laboratories Inc. (Toronto, ON). This fusion peptide was used at 50 µg/dose. Where indicated, R9F was used as an antigen (25 µg/dose) or in cytotoxicity assays. The peptide KYMCNSSCM (SEQ ID NO: 13) (Dalton) was used as an irrelevant control peptide.

The tyrosinase-related protein (TRP-2) peptides S9L (amino acids 180-188; SVYDFFVWL; SEQ ID NO: 7) and V8L (amino acids 181-188; VYDFFVWL; SEQ ID NO: 6), as well as the p53 peptides (wild type p53 (K9M), amino acids 232-240; KYMCNSSCM; SEQ ID NO: 9), modified p53 peptide mK9M (amino acids 232-240; KYICNSSCM; SEQ ID NO: 8) and mK9M coupled to PADRE (AKXVAAWTLKAAAKYICNSSCM; SEQ ID NO: 17) were purchased from Dalton Chemical Laboratories, Inc. (Toronto, ON, Canada). These peptides are presented by the murine MHC-class I H-2K. S9L is also presented by MHC HLA A2, whereas, V8L is not presented by MHC HLA A2. The TRP2 and p53 peptides were stored as a 1 mg/ml stock solution in DMSO. Further dilutions for vaccine manufacture were made using PBS.

All formulations of the vaccines, except those containing coupled mK9M, contained PADRE (25 µg/dose) and CpG ODN 1826 (50 μg/dose). Coupled mK9M contained PADRE as part of its structure, therefore, addition of free PADRE was unnecessary.

The amino acid sequence of the irrelevant peptide used in ELISPOT determinations was KIMCNSSCM (Dalton Chemical Laboratories Inc.).

Adjuvants

CpG ODN (Synthetic ODN 1826 with CpG motifs underlined (SEQ ID NO: 12)
5'-TCCAT<u>GACGTT</u>CCT<u>GACGTT</u>-3', 50 μg/dose)

was obtained from Coley Pharmaceutical (Wellesley, Mass.). Lipopetide (Pam3Cys-SKKKK, (100 μg/dose) was obtained from EMC Microcollections, Germany.

Treatments

Liposomes were prepared as follows; lecithin and cholesterol in a ratio of 10:1 (0.2 g lecithin and 0.02 g cholesterol/dose) were dissolved in chloroform/methanol (1:1; v/v) and the solution filter-sterilized using a PTFE 0.2 μm filter. Chloroform and methanol were removed under reduced pressure using a rotary evaporator and traces of the solvents were further removed from the resulting thin lipid layer in vacuo. For liposome encapsulation, fusion peptides with CpG were dissolved in sterile PBS and the resulting solution added to the thin lipid layer with mixing to form liposomes. The resulting suspension of liposomes was emulsified in FIA (Sigma, St Louis, Mo.) by adding the liposome/PBS suspension to FIA to form a water-in-oil emulsion (PBS: FIA; 1:1, v/v; 100 μl/dose). In some experiments, Montanide ISA51 (Seppic, France) was used in place of FIA as the oil carrier.

Pathogen-free C57BL/6 female mice, 6-8 weeks of age, were obtained from Charles River Laboratories (Wilmington, Mass.) and were housed under filter top conditions with water and food ad libitum. Institutional animal care and use guidelines were followed for all experiments. Mice were treated with compositions of the invention by subcutaneous injection at the base of the tail. Unless stated otherwise, all treatments were single administration and all treatment groups contained 10 mice. Control mice were injected subcutaneously with PBS or a fusion peptide (a selected CTL epitope fused to PADRE), R9F peptide, CpG ODN (or Pam3c), fusion peptide with CpG in PBS (100 μl) or liposome encapsulated fusion peptide, R9F, CpG (or Pam3c) in a water-in-oil emulsion (PBS/FIA; 1:1, v/v, 100 μl/dose).

Tumor Implantation

C3 cells used in tumor implantation were grown to 95% confluency and harvested with 0.05% trypsin. To establish tumors in mice, mice were injected with $0.5 \times 10^6$ C3 cells s. c. in the left flank. Tumor sizes were determined every 4-5 days using the following formula: longest measurement× (shortest measurement)$^2$ divided by 2.

Mice (HLA A2) were challenged with TC1/A2 tumor cells ($1 \times 10^5$ cells/mouse) implanted subcutaneously in the left flank. Tumor size was measured every 5 days and is reported as tumor size in individual mice and as percent tumor bearing mice.

B16-F10 cells ($10 \times 10^3$ cells/mouse) were implanted subcutaneously in the left flank of pathogen-free C57BL/6 mice that were 6-8 weeks of age at time of challenge. Tumor size was measured every 2-5 days and the results reported as percent tumor bearing mice.

Cytotoxicity Assays

CTL assays, ELISPOT and intracellular staining for interferon (IFN)-γ showed the therapeutic response was specific for the selected E7 peptide since an irrelevant peptide did not elicit CTL activity or IFN-γ production above background. These studies indicate that increases in activated treatment-specific cytotoxic T-cells in splenocytes from mice given the therapeutic treatment correlate with tumor size reduction. Details of the procedures used are described below.

Lymphoblast Generation and in-vitro Stimulation (IVS)

To examine the acute and memory CTL response, splenocytes from treated mice were analyzed 7, 14 or 130 days post-immunization respectively, unless stated otherwise. Where stated, the cytotoxicity assay was performed upon one round of IVS. Briefly, three days before in vitro stimulation, naïve C57BL/6 mice were sacrificed by $CO_2$ asphyxiation and spleens were harvested and disassociated. Splenocytes were washed and counted in RPMI-10 where RPMI is supplemented with 10% heat-inactivated fetal calf serum (Sigma, St Louis, Mo.), 50 mM 2-mercaptoethanol (Gibco), 100 U/ml penicillin and 100 □g/ml streptomycin (Gibco). Splenocytes ($10^6$ cells/ml) were cultured with lipopolysaccharide (25 μg/ml) and dextran sulphate (7 μg/ml) treated lymphoblasts.

Syngeneic lymphoblasts were irradiated (by 4000 rad using a $^{137}$Sc source for 15 minutes) and loaded with the R9F peptide (100 μM). Peptide-loaded LPS activated lymphoblasts ($3 \times 10^6$ cells/ml) were used to stimulate splenocytes of immunized mice in a ratio of 3:1 where effector cells were adjusted to $3 \times 10^6$ cells/ml, and T-stim (BD Biosciences, Mississauga, ON) was added to wells to obtain a final concentration of 20%. Cells were incubated at 37° C./5% $CO_2$ for 6 days.

JAM Assay

EL-4 cells were labeled with 5 μCi/ml [Methyl-$^3$H] thymidine (Amersham Pharmacia, Erlangen, Germany). The cells were incubated at 37° C./5% $CO_2$ for 24 hours then loaded with R9F or irrelevant peptides (10 μg/ml) for one hour. Suspensions of labelled target cells were then harvested, washed twice in RPMI-10, and seeded in 96-well U-bottom plates at a density of $2 \times 10^3$ cells/well. The effector cells were added by serial dilution starting at a concentration of $2 \times 10^5$ effector cells/well. The plates were incubated for 4 hours at 37° C./5% $CO_2$. The cells were aspirated onto fiberglass filters and tritium counted using a Packard Top-Count scintillation counter. The percent DNA fragmentation was calculated using the following formula: % DNA fragmentation=(S−E)/E×100, where S is retained DNA (counts) in the absence of treatment (spontaneous) and E is retained DNA (counts) in the presence of effector cells.

Ex vivo Analysis of Antigen-specific T Cells by ELISPOT

Activated antigen-specific CTLs in splenocytes harvested from treated C57BL/6 mice were detected using a BD ELISPOT (BD Bioscience, San Diego, Calif.). Briefly, on day 7 post-treatment a 96-well nitrocellulose plate was coated with the capture antibody, a purified anti-mouse IFN-γ antibody, and incubated overnight at 4° C. The antibody was discarded and the plate was blocked for 2 hours then the blocking solution was removed. Splenocytes were each added to their respective wells at an initial concentration of 1 million cells/well in a final volume of 100 μl followed by serial dilutions in subsequent wells of a row. The following stimulators and controls were added to 100 μl of media to obtain their desired final concentration. Either, C3 cells ($5 \times 10^5$ cells/ml), the R9F peptide (10 μg/ml), the irrelevant peptide (10 μg/ml), or no peptides were added to the wells. PMA (5 ng/ml, Sigma), ionomycin (500 ng/ml, Sigma), served as positive controls and the irrelevant peptide and media alone served as negative controls. The plate was incubated overnight at 37° C./5% $CO_2$ after which the detection antibody, a biotinylated anti-mouse IFN-γ antibody, was added for 2 hours at room temperature. Following the incubation period, the detection antibody was discarded and the enzyme conjugate (Streptavidin-HRP) was added for 1 hour and lastly the plate was stained with an AEC substrate solution for 20 minutes. The plate was washed and left to air dry overnight for visualization of spots using a magnifying lens.

Intracellular Cytokine Staining (ICS)

Splenocytes were retrieved from spleens of tumor-free mice as previously described, washed twice with RPMI-10 (500×g, 5 minutes) and resuspended in RMPI-10 ($10 \times 10^6$ cells/ml). Splenocytes ($1 \times 10^6$ cells/well) were added to wells of a 96-well flat bottom plate and incubated with R9F or an irrelevant peptide at a final concentration of 3 µg/ml in duplicate columns for each peptide. In experiments that used EL-4 cells to demonstrate the protective function of IFNγ-producing $CD8^+$ CTLs, EL-4 cells ($1 \times 10^5$ cells/well) loaded with either R9F or the irrelevant peptide were incubated for 6 hours at 37° C./5% $CO_2$ before cytotoxicity measurements.

Intracellular cytokine staining was performed as described in the Cytofix™/Cytoperm™ kit instruction manual (BD Biosciences, Mississauga, ON). In brief, after addition of stimulants, GolgiStop was added to each well and the plates were incubated (37° C./5% $CO_2$) for 4 hours. Cells were washed with staining buffer then incubated (20 minutes at 4° C., in the dark) with anti-CD8 serum, washed again with staining buffer followed by incubation with anti-IFN-γ (30 minutes at 4° C. in the dark). This was followed by washes with perm/wash buffer after which cells were resuspended with perm/wash buffer and transferred to FACS tubes (BD Falcon). Staining was assessed by FACSCalibur (BD Biosciences, San Jose, Calif.), and data were analysed using CellQuest software.

REFERENCES

Allegra, C. J. and R. W. Childs, Cytotoxins and cancer immunotherapy: The dance of the macabre. J. National Cancer Institute, 97:1396-1397, 2005.

Antonia, S. J. et al., Combination of p53 cancer vaccine with chemotherapy in patients with extensive stage small cell lung cancer. Clinical Cancer Research, 12:878-887, 2006.

Bellone, M. et al., Relevance of the tumor antigen in the validation of three vaccination strategies for melanoma, *Journal of Immunology*, 165(5):2651-6, 2000.

Bronte, V. et al., Genetic Vaccination with "Self" Tyrosinase-related Protein 2 Causes Melanoma Eradication but not Vitiligo, *Cancer Research*, 60:253-258, Jan. 15, 2000.

Celis E. et al., Recognition of hepatitis B surface antigen by human T lymphocytes. Proliferative and cytotoxic responses to a major antigenic determinant defined by synthetic peptides, *Journal of Immunology*, 140:1808-1815, 1988.

Chakraborty, M. et al., External beam radiation of tumors alters phenotype of tumor cells to render them susceptible to vaccine-mediated T-cell killing. Cancer Research, 64:4328-4337, 2004.

Chong P. et al., Identification of T- and B-cell epitopes of the S2 and S3 subunits of pertussis toxin by use of synthetic peptides, *Infection and Immunity*, 60:4640-4647, 1992.

Correale, P. et al, Fluorouracil-based chemotherapy enhances the antitumor activity of a thymidylate synthase-directed polyepitopic peptide vaccine. Journal of the National Cancer Institute 97:1437-1445, 2005.

DeLeo, A. B., p53-based immunotherapy of cancer, *Critical Reviews in Immunology*, 18:29, 1998.

Demotz S. et al., Delineation of several DR-restricted tetanus toxin T cell epitopes, *Journal of Immunology*, 142: 394-402, 1989.

Diethelm-Okita, B. M. et al., Universal epitopes for human $CD4^+$ cells on tetanus and diphtheria toxins. *Journal of Infectious Diseases*, 181:1001-1009, 2000.

Dudley, M. E. et al., Adoptive transfer of cloned melanoma-reactive T lymphocytes for the treatment of patients with metastatic melanoma, *Journal of Immunotherapy*, 24(4): 363-73 2001.

Fernando, G. J. et al., Vaccine-induced Th1-type responses are dominant over Th2-type responses in the short term whereas pre-existing Th2 responses are dominant in the longer term. *Scandinavian Journal of Immunology*, 47(5): 459-65, 1998.

Frezard, F., Liposomes: From biophysics to the design of peptide vaccines. *Brazilian Journal Medical Biology Research*, 32:181-189, 1999.

Gregoriadis, G., Immunological adjuvants: A role for liposomes, *Immunology Today*, 11:89-97, 1990.

Gulley, J. L. et al., Combining a recombinant cancer vaccine with standard definitive radiotherapy in patients with localized prostate cancer. Clinical Cancer Research, 11: 3353-3362, 2005.

Knutson, K. L., et al., Immunization of cancer patients with a HER-2/neu, HLA-A2 peptide, p369-377, results in short-lived peptide-specific immunity." *Clinical Cancer Research*, 8(5): 1014-8, 2002.

Pilon-Thomas, S. et al., Immunostimulatory Effects of CpG-ODN Upon Dendritic Cell-Based Immunotherapy in a Murine Melanoma Model, *Journal Immunotherapy*, 29(4), July/August 2006.

Vierboom, M. P. M. et al., p53: a target for T-cell mediated immunotherapy, *Peptide-Based Cancer Vaccines*, W. M. Kast, Ed. Landes Bioscience, Georgetown, p. 40, 2000.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

The invention claimed is:

1. A method for inducing an enhanced cytotoxic T lymphocyte (CTL) response thereby treating cancer or inhibiting or preventing the growth or proliferation of cancer cells in a subject in need of cancer treatment comprising administering a composition comprising:
   a carrier consisting essentially of oil or which is a water-in-oil emulsion, wherein the oil is mineral oil, nut oil or squalene;
   liposomes;
   at least one antigen comprising a CTL epitope; and
   at least one T helper epitope:
   wherein the antigen and the T helper epitope are encapsulated within said liposomes.

2. The method of claim 1 wherein the cancer is selected from the group consisting of: cervical, vulvar, melanoma, breast, lung, ovarian, multiple myelomna, B cell lymphoma, hepatoma, sarcoma, bladder, prostate cancer, thyroid, H/N tumors, colon, rectal, renal, pancreatic, gastric, adenocarcinoma, T cell leukemia, lymphosarcoma, uterine, esophageal, non-Hodgkin's lymphomas, endometrial, and RCC tumors.

3. The method of claim 1, wherein said T helper epitope is a separate molecule from said antigen.

4. The method of claim 1, wherein said antigen comprises said T helper epitope or wherein said antigen is fused to said T helper epitope.

5. The method of claim 1, wherein said antigen comprises combination of CTL epitopes.

6. The method of claim 1, wherein said CTL epitope is derived from a tumor-associated protein.

* * * * *

SEQUENCE LISTING

<160> NUMBER OF SEQ ID NOS: 56

<210> SEQ ID NO 1
<211> LENGTH: 9
<212> TYPE: PRT
<213> ORGANISM: Human papillomavirus

<400> SEQUENCE: 1

Arg Ala His Tyr Asn Ile Val Thr Phe
1               5

<210> SEQ ID NO 2
<211> LENGTH: 10
<212> TYPE: PRT
<213> ORGANISM: Human papillomavirus

<400> SEQUENCE: 2

Tyr Met Leu Asp Leu Gln Pro Glu Thr Thr
1               5                   10

<210> SEQ ID NO 3
<211> LENGTH: 9
<212> TYPE: PRT
<213> ORGANISM: Human papillomavirus

<400> SEQUENCE: 3

Leu Leu Met Gly Thr Leu Gly Ile Val
1               5

<210> SEQ ID NO 4
<211> LENGTH: 8
<212> TYPE: PRT
<213> ORGANISM: Human papillomavirus

<400> SEQUENCE: 4

Thr Leu Gly Ile Val Cys Pro Ile
1               5

<210> SEQ ID NO 5
<211> LENGTH: 10
<212> TYPE: PRT
<213> ORGANISM: Human papillomavirus

<400> SEQUENCE: 5

Thr Ile His Asp Ile Ile Leu Glu Cys Val
1               5                   10

<210> SEQ ID NO 6
<211> LENGTH: 8
<212> TYPE: PRT
<213> ORGANISM: Unknown
<220> FEATURE:
<223> OTHER INFORMATION: Melanoma-related antigen

<400> SEQUENCE: 6

Val Tyr Asp Phe Phe Val Trp Leu
1               5

<210> SEQ ID NO 7
<211> LENGTH: 9
<212> TYPE: PRT
<213> ORGANISM: Unknown
<220> FEATURE:
<223> OTHER INFORMATION: Melanoma-related antigen

<400> SEQUENCE: 7

```
Ser Val Tyr Asp Phe Phe Val Trp Leu
1               5

<210> SEQ ID NO 8
<211> LENGTH: 9
<212> TYPE: PRT
<213> ORGANISM: Unknown
<220> FEATURE:
<223> OTHER INFORMATION: Melanoma-related antigen

<400> SEQUENCE: 8

Lys Tyr Ile Cys Asn Ser Ser Cys Met
1               5

<210> SEQ ID NO 9
<211> LENGTH: 9
<212> TYPE: PRT
<213> ORGANISM: Unknown
<220> FEATURE:
<223> OTHER INFORMATION: Melanoma-associated antigen

<400> SEQUENCE: 9

Lys Tyr Met Cys Asn Ser Ser Cys Met
1               5

<210> SEQ ID NO 10
<211> LENGTH: 13
<212> TYPE: PRT
<213> ORGANISM: Unknown
<220> FEATURE:
<223> OTHER INFORMATION: Universal T-helper epitope (PADRE)
<220> FEATURE:
<221> NAME/KEY: misc_feature
<222> LOCATION: (3)..(3)
<223> OTHER INFORMATION: Xaa= cyclohexylalanyl

<400> SEQUENCE: 10

Ala Lys Xaa Val Ala Ala Trp Thr Leu Lys Ala Ala Ala
1               5                   10

<210> SEQ ID NO 11
<211> LENGTH: 21
<212> TYPE: PRT
<213> ORGANISM: Unknown
<220> FEATURE:
<223> OTHER INFORMATION: T-helper epitope (F21E)

<400> SEQUENCE: 11

Phe Asn Asn Phe Thr Val Ser Phe Trp Leu Arg Val Pro Lys Val Ser
1               5                   10                  15

Ala Ser His Leu Glu
            20

<210> SEQ ID NO 12
<211> LENGTH: 20
<212> TYPE: DNA
<213> ORGANISM: Unknown
<220> FEATURE:
<223> OTHER INFORMATION: CpG oligodeoxynucleotide for use as adjuvant

<400> SEQUENCE: 12
tccatgacgt tcctgacgtt                                           20

<210> SEQ ID NO 13
<211> LENGTH: 9
<212> TYPE: PRT
```

```
<213> ORGANISM: Artificial
<220> FEATURE:
<223> OTHER INFORMATION: Irrelevant Control Peptide

<400> SEQUENCE: 13

Lys Ile Met Cys Asn Ser Ser Cys Met
1               5

<210> SEQ ID NO 14
<211> LENGTH: 46
<212> TYPE: PRT
<213> ORGANISM: Unknown
<220> FEATURE:
<223> OTHER INFORMATION: linked peptide: human papillomavirus sequence
      linked by amino acids AAY

<400> SEQUENCE: 14

Thr Ile His Asp Ile Ile Leu Glu Cys Val Ala Ala Tyr Tyr Met Leu
1               5                   10                  15

Asp Leu Gln Pro Glu Thr Thr Ala Ala Tyr Leu Leu Met Gly Thr Leu
            20                  25                  30

Gly Ile Val Ala Ala Tyr Thr Leu Gly Ile Val Cys Pro Ile
        35                  40                  45

<210> SEQ ID NO 15
<211> LENGTH: 22
<212> TYPE: PRT
<213> ORGANISM: Unknown
<220> FEATURE:
<223> OTHER INFORMATION: Dipeptide: human papillomavirus sequence by
      amino acids KKP

<400> SEQUENCE: 15

Thr Ile His Asp Ile Ile Leu Glu Cys Val Lys Lys Pro Leu Leu Met
1               5                   10                  15

Gly Thr Leu Gly Ile Val
            20

<210> SEQ ID NO 16
<211> LENGTH: 21
<212> TYPE: PRT
<213> ORGANISM: Unknown
<220> FEATURE:
<223> OTHER INFORMATION: Dipeptide: human papillomavirus sequence linked
      by amino acids KKP

<400> SEQUENCE: 16

Thr Leu Gly Ile Val Cys Pro Ile Lys Lys Pro Tyr Met Leu Asp Leu
1               5                   10                  15

Gln Pro Glu Thr Thr
            20

<210> SEQ ID NO 17
<211> LENGTH: 22
<212> TYPE: PRT
<213> ORGANISM: Unknown
<220> FEATURE:
<223> OTHER INFORMATION: Universal T-helper epitope (PADRE) coupled to
      mK9M p53 epitope
<220> FEATURE:
<221> NAME/KEY: misc_feature
<222> LOCATION: (3)..(3)
<223> OTHER INFORMATION: Xaa= cycloheyxlalanyl

<400> SEQUENCE: 17

Ala Lys Xaa Val Ala Ala Trp Thr Leu Lys Ala Ala Ala Lys Tyr Ile
```

```
1               5                   10                  15

Cys Asn Ser Ser Cys Met
                20

<210> SEQ ID NO 18
<211> LENGTH: 9
<212> TYPE: PRT
<213> ORGANISM: Unknown
<220> FEATURE:
<223> OTHER INFORMATION: Mart-1/Melan-A: melanoma antigen recognized by
      T cells

<400> SEQUENCE: 18

Ala Ala Gly Ile Gly Ile Leu Thr Val
1               5

<210> SEQ ID NO 19
<211> LENGTH: 10
<212> TYPE: PRT
<213> ORGANISM: Unknown
<220> FEATURE:
<223> OTHER INFORMATION: Mart-1/Melan-A: melanoma antigen recognized by
      T cells

<400> SEQUENCE: 19

Glu Ala Ala Gly Ile Gly Ile Leu Thr Val
1               5                   10

<210> SEQ ID NO 20
<211> LENGTH: 9
<212> TYPE: PRT
<213> ORGANISM: Unknown
<220> FEATURE:
<223> OTHER INFORMATION: Mart-1/Melan-A: melanoma antigen recognized by
      T cells

<400> SEQUENCE: 20

Ile Leu Thr Val Ile Leu Gly Val Leu
1               5

<210> SEQ ID NO 21
<211> LENGTH: 10
<212> TYPE: PRT
<213> ORGANISM: Unknown
<220> FEATURE:
<223> OTHER INFORMATION: Mart-1/Melan-A: melanoma antigen recognized by
      T cells

<400> SEQUENCE: 21

Ala Glu Glu Ala Ala Gly Ile Gly Ile Leu
1               5                   10

<210> SEQ ID NO 22
<211> LENGTH: 11
<212> TYPE: PRT
<213> ORGANISM: Unknown
<220> FEATURE:
<223> OTHER INFORMATION: Mart-1/Melan-A: melanoma antigen recognized by
      T cells

<400> SEQUENCE: 22

Ala Glu Glu Ala Ala Gly Ile Gly Ile Leu Thr
1               5                   10

<210> SEQ ID NO 23
<211> LENGTH: 9
<212> TYPE: PRT
```

```
<213> ORGANISM: Unknown
<220> FEATURE:
<223> OTHER INFORMATION: MC1R: Melanocortin 1 receptor

<400> SEQUENCE: 23

Thr Ile Leu Leu Gly Ile Phe Phe Leu
1               5

<210> SEQ ID NO 24
<211> LENGTH: 9
<212> TYPE: PRT
<213> ORGANISM: Unknown
<220> FEATURE:
<223> OTHER INFORMATION: MC1R: Melanocortin 1 receptor

<400> SEQUENCE: 24

Phe Leu Ala Leu Ile Ile Cys Asn Ala
1               5

<210> SEQ ID NO 25
<211> LENGTH: 9
<212> TYPE: PRT
<213> ORGANISM: Unknown
<220> FEATURE:
<223> OTHER INFORMATION: Gp100: melanocyte associated antigen

<400> SEQUENCE: 25

Lys Thr Trp Gly Gln Tyr Trp Gln Val
1               5

<210> SEQ ID NO 26
<211> LENGTH: 10
<212> TYPE: PRT
<213> ORGANISM: Unknown
<220> FEATURE:
<223> OTHER INFORMATION: Gp100: melanocyte associated antigen

<400> SEQUENCE: 26

Ala Met Leu Gly Thr His Thr Met Glu Val
1               5                   10

<210> SEQ ID NO 27
<211> LENGTH: 9
<212> TYPE: PRT
<213> ORGANISM: Unknown
<220> FEATURE:
<223> OTHER INFORMATION: Gp100: melanocyte associated antigen

<400> SEQUENCE: 27

Met Leu Gly Thr His Thr Met Glu Val
1               5

<210> SEQ ID NO 28
<211> LENGTH: 10
<212> TYPE: PRT
<213> ORGANISM: Unknown
<220> FEATURE:
<223> OTHER INFORMATION: Gp100: melanocyte associated antigen

<400> SEQUENCE: 28

Ser Leu Ala Asp Thr Asn Ser Leu Ala Val
1               5                   10

<210> SEQ ID NO 29
<211> LENGTH: 9
<212> TYPE: PRT
<213> ORGANISM: Unknown
```

```
<220> FEATURE:
<223> OTHER INFORMATION: Gp100: melanocyte associated antigen

<400> SEQUENCE: 29

Ile Thr Asp Gln Val Pro Phe Ser Val
1               5

<210> SEQ ID NO 30
<211> LENGTH: 10
<212> TYPE: PRT
<213> ORGANISM: Unknown
<220> FEATURE:
<223> OTHER INFORMATION: Gp100: melanocyte associated antigen

<400> SEQUENCE: 30

Leu Leu Asp Gly Thr Ala Thr Leu Arg Leu
1               5                   10

<210> SEQ ID NO 31
<211> LENGTH: 9
<212> TYPE: PRT
<213> ORGANISM: Unknown
<220> FEATURE:
<223> OTHER INFORMATION: Gp100: melanocyte associated antigen

<400> SEQUENCE: 31

Tyr Leu Glu Pro Gly Pro Val Thr Ala
1               5

<210> SEQ ID NO 32
<211> LENGTH: 10
<212> TYPE: PRT
<213> ORGANISM: Unknown
<220> FEATURE:
<223> OTHER INFORMATION: Gp100: melanocyte associated antigen

<400> SEQUENCE: 32

Val Leu Tyr Arg Tyr Gly Ser Phe Ser Val
1               5                   10

<210> SEQ ID NO 33
<211> LENGTH: 9
<212> TYPE: PRT
<213> ORGANISM: Unknown
<220> FEATURE:
<223> OTHER INFORMATION: Gp100: melanocyte associated antigen

<400> SEQUENCE: 33

Arg Leu Pro Arg Ile Phe Cys Ser Cys
1               5

<210> SEQ ID NO 34
<211> LENGTH: 9
<212> TYPE: PRT
<213> ORGANISM: Unknown
<220> FEATURE:
<223> OTHER INFORMATION: Gp100: melanocyte associated antigen

<400> SEQUENCE: 34

Leu Ile Tyr Arg Arg Arg Leu Met Lys
1               5

<210> SEQ ID NO 35
<211> LENGTH: 9
<212> TYPE: PRT
<213> ORGANISM: Unknown
<220> FEATURE:
```

```
<223> OTHER INFORMATION: Gp100: melanocyte associated antigen

<400> SEQUENCE: 35

Ala Leu Asn Phe Pro Gly Ser Gln Lys
1               5

<210> SEQ ID NO 36
<211> LENGTH: 10
<212> TYPE: PRT
<213> ORGANISM: Unknown
<220> FEATURE:
<223> OTHER INFORMATION: Gp100: melanocyte associated antigen

<400> SEQUENCE: 36

Ser Leu Ile Tyr Arg Arg Arg Leu Met Lys
1               5                   10

<210> SEQ ID NO 37
<211> LENGTH: 9
<212> TYPE: PRT
<213> ORGANISM: Unknown
<220> FEATURE:
<223> OTHER INFORMATION: Gp100: melanocyte associated antigen

<400> SEQUENCE: 37

Ala Leu Leu Ala Val Gly Ala Thr Lys
1               5

<210> SEQ ID NO 38
<211> LENGTH: 9
<212> TYPE: PRT
<213> ORGANISM: Unknown
<220> FEATURE:
<223> OTHER INFORMATION: Gp100: melanocyte associated antigen

<400> SEQUENCE: 38

Ala Leu Leu Ala Val Gly Ala Thr Lys
1               5

<210> SEQ ID NO 39
<211> LENGTH: 9
<212> TYPE: PRT
<213> ORGANISM: Unknown
<220> FEATURE:
<223> OTHER INFORMATION: Gp100: melanocyte associated antigen

<400> SEQUENCE: 39

Val Tyr Phe Phe Leu Pro Asp His Leu
1               5

<210> SEQ ID NO 40
<211> LENGTH: 8
<212> TYPE: PRT
<213> ORGANISM: Unknown
<220> FEATURE:
<223> OTHER INFORMATION: Gp100: melanocyte associated antigen

<400> SEQUENCE: 40

Ser Asn Asp Gly Pro Thr Leu Ile
1               5

<210> SEQ ID NO 41
<211> LENGTH: 10
<212> TYPE: PRT
<213> ORGANISM: Unknown
<220> FEATURE:
<223> OTHER INFORMATION: PSA: prostate specific antigen
```

<400> SEQUENCE: 41

Val Ser His Ser Phe Pro His Pro Leu Tyr
1               5                   10

<210> SEQ ID NO 42
<211> LENGTH: 10
<212> TYPE: PRT
<213> ORGANISM: Unknown
<220> FEATURE:
<223> OTHER INFORMATION: PSA: prostate specific antigen

<400> SEQUENCE: 42

Phe Leu Thr Pro Lys Lys Leu Gln Cys Val
1               5                   10

<210> SEQ ID NO 43
<211> LENGTH: 10
<212> TYPE: PRT
<213> ORGANISM: Unknown
<220> FEATURE:
<223> OTHER INFORMATION: PSA: prostate specific antigen

<400> SEQUENCE: 43

Val Ile Ser Asn Asp Val Cys Ala Gln Val
1               5                   10

<210> SEQ ID NO 44
<211> LENGTH: 10
<212> TYPE: PRT
<213> ORGANISM: Unknown
<220> FEATURE:
<223> OTHER INFORMATION: PSM: prostate specific membrane antigen

<400> SEQUENCE: 44

His Ser Thr Asn Gly Val Thr Arg Ile Tyr
1               5                   10

<210> SEQ ID NO 45
<211> LENGTH: 9
<212> TYPE: PRT
<213> ORGANISM: Unknown
<220> FEATURE:
<223> OTHER INFORMATION: Tyrosinase

<400> SEQUENCE: 45

Lys Cys Asp Ile Cys Thr Asp Glu Tyr
1               5

<210> SEQ ID NO 46
<211> LENGTH: 11
<212> TYPE: PRT
<213> ORGANISM: Unknown
<220> FEATURE:
<223> OTHER INFORMATION: Tyrosinase

<400> SEQUENCE: 46

Ser Ser Asp Tyr Val Ile Pro Ile Gly Thr Tyr
1               5                   10

<210> SEQ ID NO 47
<211> LENGTH: 9
<212> TYPE: PRT
<213> ORGANISM: Unknown
<220> FEATURE:
<223> OTHER INFORMATION: Tyrosinase

```
<400> SEQUENCE: 47

Tyr Met Asp Gly Thr Met Ser Gln Val
1               5

<210> SEQ ID NO 48
<211> LENGTH: 9
<212> TYPE: PRT
<213> ORGANISM: Unknown
<220> FEATURE:
<223> OTHER INFORMATION: Tyrosinase

<400> SEQUENCE: 48

Met Leu Leu Ala Val Leu Tyr Cys Leu
1               5

<210> SEQ ID NO 49
<211> LENGTH: 9
<212> TYPE: PRT
<213> ORGANISM: Unknown
<220> FEATURE:
<223> OTHER INFORMATION: Tyrosinase

<400> SEQUENCE: 49

Ala Phe Leu Pro Trp His Arg Leu Phe
1               5

<210> SEQ ID NO 50
<211> LENGTH: 9
<212> TYPE: PRT
<213> ORGANISM: Unknown
<220> FEATURE:
<223> OTHER INFORMATION: Tyrosinase

<400> SEQUENCE: 50

Ser Glu Ile Trp Arg Asp Ile Asp Phe
1               5

<210> SEQ ID NO 51
<211> LENGTH: 9
<212> TYPE: PRT
<213> ORGANISM: Unknown
<220> FEATURE:
<223> OTHER INFORMATION: Tyrosinase

<400> SEQUENCE: 51

Met Ser Leu Gln Arg Gln Phe Leu Arg
1               5

<210> SEQ ID NO 52
<211> LENGTH: 9
<212> TYPE: PRT
<213> ORGANISM: Unknown
<220> FEATURE:
<223> OTHER INFORMATION: TRP1: tyrosinase related protein 1

<400> SEQUENCE: 52

Ser Val Tyr Asp Phe Phe Val Trp Leu
1               5

<210> SEQ ID NO 53
<211> LENGTH: 9
<212> TYPE: PRT
<213> ORGANISM: Unknown
<220> FEATURE:
<223> OTHER INFORMATION: TRP2: tyrosinase related protein 2

<400> SEQUENCE: 53
```

```
Thr Leu Asp Ser Gln Val Met Ser Leu
1               5

<210> SEQ ID NO 54
<211> LENGTH: 9
<212> TYPE: PRT
<213> ORGANISM: Unknown
<220> FEATURE:
<223> OTHER INFORMATION: TRP2: tyrosinase related protein 2

<400> SEQUENCE: 54

Leu Leu Gly Pro Gly Arg Pro Tyr Arg
1               5

<210> SEQ ID NO 55
<211> LENGTH: 9
<212> TYPE: PRT
<213> ORGANISM: Unknown
<220> FEATURE:
<223> OTHER INFORMATION: p53

<400> SEQUENCE: 55

Ala Asn Asp Pro Ile Phe Val Val Leu
1               5

<210> SEQ ID NO 56
<211> LENGTH: 5
<212> TYPE: PRT
<213> ORGANISM: Unknown
<220> FEATURE:
<223> OTHER INFORMATION: Pam3Cys Lipopeptide

<400> SEQUENCE: 56

Ser Lys Lys Lys Lys
1               5
```